US012125299B2

(12) United States Patent
Van Der Horst

(10) Patent No.: US 12,125,299 B2
(45) Date of Patent: Oct. 22, 2024

(54) DETERMINING INTERACTIONS BETWEEN CELLS BASED ON FORCE SPECTROSCOPY

(71) Applicant: LUMICKS CA HOLDING B.V., Amsterdam (NL)

(72) Inventor: Jelle Van Der Horst, Amsterdam (NL)

(73) Assignee: LUMICKS CA HOLDING B.V. (NL)

( * ) Notice: Subject to any disclaimer, the term of this patent is extended or adjusted under 35 U.S.C. 154(b) by 365 days.

(21) Appl. No.: 17/755,610

(22) PCT Filed: Nov. 4, 2020

(86) PCT No.: PCT/EP2020/081017
§ 371 (c)(1),
(2) Date: May 3, 2022

(87) PCT Pub. No.: WO2021/089654
PCT Pub. Date: May 14, 2021

(65) Prior Publication Data
US 2022/0366708 A1    Nov. 17, 2022

(30) Foreign Application Priority Data
Nov. 4, 2019   (NL) ...................................... 2024155

(51) Int. Cl.
*G06V 20/69*   (2022.01)
*G06T 7/00*    (2017.01)
(Continued)

(52) U.S. Cl.
CPC .......... *G06V 20/695* (2022.01); *G06T 7/0016* (2013.01); *G06T 7/70* (2017.01); *G06V 10/751* (2022.01); *G06T 2207/10056* (2013.01)

(58) Field of Classification Search
CPC ...... G06V 20/695; G06V 10/751; G06T 7/70; G06T 7/0016; G06T 2207/10056
(Continued)

(56) References Cited

U.S. PATENT DOCUMENTS 8,795,143 B2    8/2014  Wong et al.
9,677,109 B2 *  6/2017  Shamsheyeva .......... G16B 5/00
(Continued)

FOREIGN PATENT DOCUMENTS

WO    2014200341 A1   12/2014
WO    2017147398 A1    8/2017
(Continued)

OTHER PUBLICATIONS

International Search Report and Written Opinion for corresponding International application No. PCT/EP2020/081017; dated Jan. 27, 2021 (17 pages).
(Continued)

*Primary Examiner* — William D Titcomb
(74) *Attorney, Agent, or Firm* — Mendelsohn Dunleavy, P.C.

(57) ABSTRACT

Methods and systems for determining interaction between cells are described wherein the method includes determining or receiving a sequence of images representing manipulating first cells, in a holding space, the holding space including a functionalized wall comprising second cells, the manipulating including settling of the first cells onto the functionalized wall and applying a force on the settled first cells; detecting groups of pixels representing first cells in first images representing the settling of the first cells onto the functionalized wall; tracking locations of detected first cells in the first images; and, determining settling events, a settling event being determined if a cell in a first image is not distinguishable from background of the first image, the location in the image at which a cell settling event is detected defining a cell settling location; detecting groups of pixels representing cells in second images captured during the application of the force and tracking locations of detected cells, wherein tracked locations of a detected cell in
(Continued)

the second images form a tracking path, the first location of the tracking path defining a pop-up event, the location in a second image at which a pop-up event is detected defining a pop-up location; and, determining detachment events based on the settling locations and based on the pop-up locations, a detachment event defining a first cell being detached from a second cell due to application of the force on the first cell, and determining information about the interaction between first and second cells based on the force applied to the first cells.

19 Claims, 14 Drawing Sheets

(51) Int. Cl.
    *G06T 7/70*     (2017.01)
    *G06V 10/75*    (2022.01)

(58) Field of Classification Search
    USPC .......................................................... 382/128
    See application file for complete search history.

(56) References Cited

U.S. PATENT DOCUMENTS

| | | | |
|---|---|---|---|
| 2011/0110577 A1* | 5/2011 | Mangoubi | G06V 20/695 |
| | | | 382/133 |
| 2017/0148186 A1* | 5/2017 | Holzer | G06T 7/337 |
| 2017/0175174 A1* | 6/2017 | Chiu | C12Q 1/6816 |
| 2018/0112173 A1* | 4/2018 | Wiles | G06T 7/0016 |
| 2019/0156516 A1* | 5/2019 | Nikkanen | H04N 23/73 |
| 2020/0090371 A1* | 3/2020 | Hu | H04N 23/30 |
| 2022/0366708 A1* | 11/2022 | Van Der Horst | G06V 10/751 |

FOREIGN PATENT DOCUMENTS

| | | |
|---|---|---|
| WO | 2018083193 A2 | 5/2018 |
| WO | 2018083193 A3 | 5/2018 |

OTHER PUBLICATIONS

Murad, Yousif, "Biophysical Investigation of Leukocyte Rolling Adhesion at the Single Cell Level." Thesis, Masters of Science, University of British Columbia (Jul. 2018): 1-113.

Jaquaman, Khuloud, et al. "Robust single-particle tracking in live-cell time-lapse sequences." Nature Methods 5.8 (2008): 695-702.

* cited by examiner

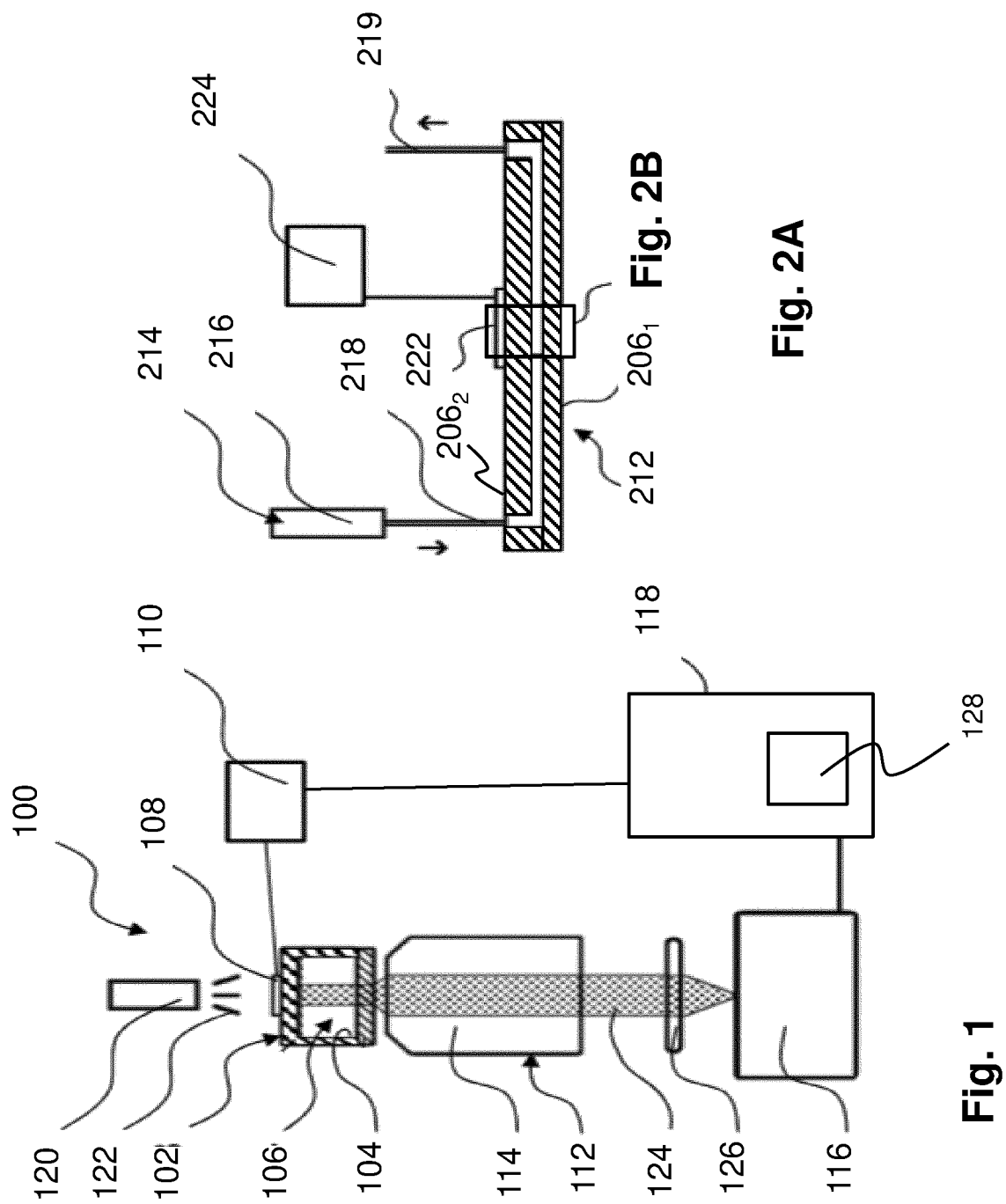

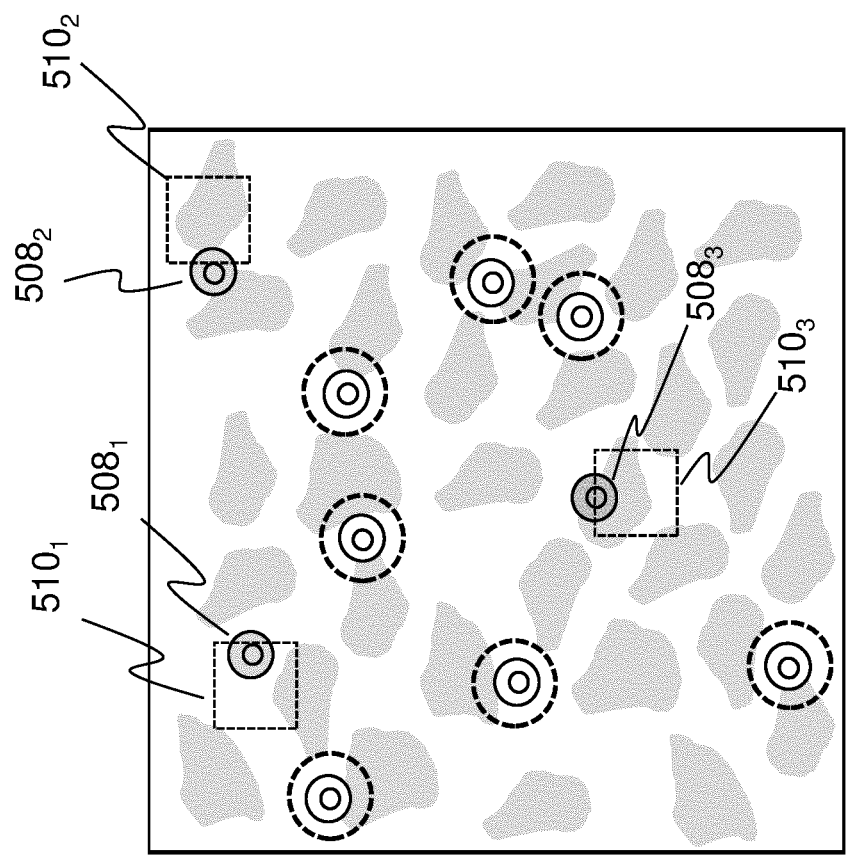
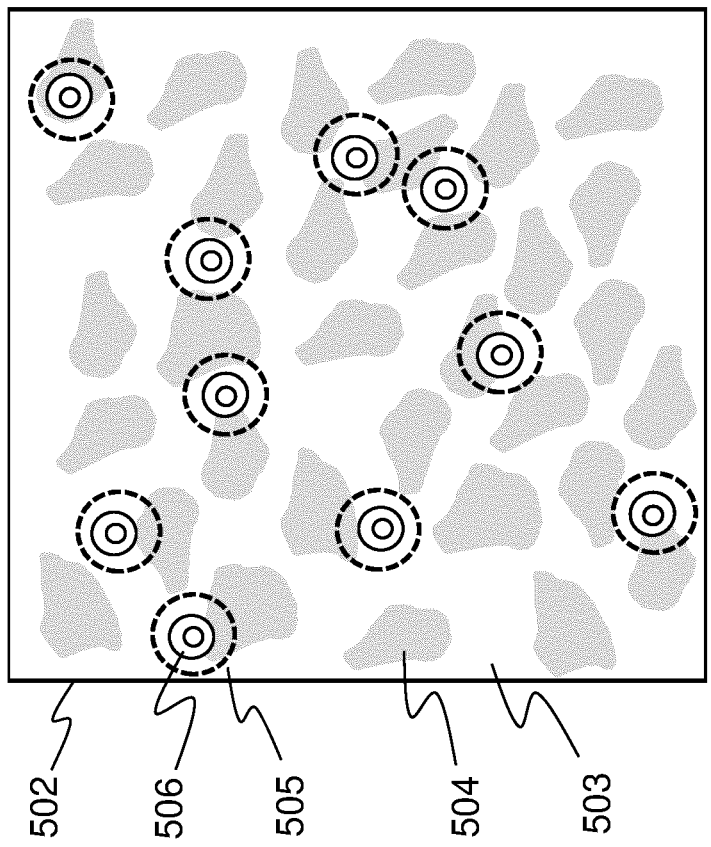
Fig. 5B
Fig. 5A

DETERMINING INTERACTIONS BETWEEN CELLS BASED ON FORCE SPECTROSCOPY

FIELD OF THE INVENTION

The disclosure relates to determining interactions between cells based on force spectroscopy and, in particular, though not exclusively, to methods and systems for determining interactions between cells based on force spectroscopy, and a computer program product enabling a computer system to perform such methods.

BACKGROUND OF THE INVENTION

The study of cell interactions, e.g. the binding strength of cells on cells is a highly relevant and active research area in biosciences. For example, the avidity characterizes the cumulative effect of multiple individual binding interactions between cells. Similarly, the affinity characterizes the strength with which a cell, e.g. an antibody, binds to a protein complex that is part of a cell membrane of a target cell. The avidity and affinity are examples of parameters that play an essential role in the study and development of therapies in medicine, e.g. immune oncology.

A technique for studying interactions between cells is referred to as force spectroscopy. For example, WO2018/083193 describes a so-called acoustic force spectroscopy AFS system that is configured to examine interactions between cells by applying a force to the cells. The system includes a microfluidic cell comprising a functionalised wall surface which may include target cells. A plurality of unlabelled effector cells, e.g. T-cells, can be flushed into the microfluidic cell, so that they can settle and bind to target cells. Thereafter, an acoustic source is used to exert a ramping force on the bound effector cells so that effector cells will detach from the target cells at a certain force. During this process, the spatiotemporal behaviour of the effector cells in the microfluidic cells is imaged using an imaging microscope. The interaction between cells, e.g. the force at which the effector cells detach, may be determined by analysing the captured video images. For example, the cell avidity of the effector cells can be determined this way.

The camera of the imaging microscope may have a focal plane essentially parallel to the functionalised wall surface so that images will typically show effector cells in the foreground against a background representing the functionalized wall that comprise the target cells. The analysis of these captured images may include detecting cells and tracking detected cells in two or three dimensions. During a typical AFS experiment, a large amount of effector cells need to be detected, accurately localized and tracked during the settling of the cells onto the functionalized wall, the binding of the effector cells to target cells (incubation) and the detachment of the effector cells from the target cells.

While cell tracking of labelled cells in conventional fluorescence microscopy is well known, automatic detection and tracking of a multitude, e.g. thousands or even tens of thousands of unlabelled effector cells against a background of a highly dynamic, "living" functionalized wall surface (a layer of target cells) during force spectroscopy is not a trivial problem. The effector cells and the target cells may be similar of size and/or shape, resulting in a very poor contrast between foreground and background, especially when the effector cells are very close to the target cells.

The contrast problem may introduce "false events" during the cell detection and tracking process and thus will further complicate the automated cell detection and tracking process. can also arise even if there is a large difference in shape and size between the target and effector cells. Moreover, during the incubation process effector cells can move over the functionalized surface to find matching target cells. Effector cells may deform and/or visually disappear when they are close to or bind to target cells or the substrate. Moreover, during the force ramping also target cells and/or debris may detach from the functionalized wall surface, which may introduce "false events" during the cell detection and tracking process and thus will further complicate the automated cell detection and tracking process.

Hence, from the above, it follows that there is a need in the art for an accurate and robust automated determining of interactions between cells based on force spectroscopy.

SUMMARY OF THE INVENTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Functions described in this disclosure may be implemented as an algorithm executed by a microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing.

Computer program code for carrying out operations for aspects of the present invention may be written in any combination of one or more programming languages, including a functional or an object oriented programming language such as Java™, Scala, C++, Python or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer, server or virtualized server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or central processing unit (CPU), or graphics processing unit (GPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

It is an objective of the embodiments in this disclosure to reduce or eliminate at least one of the drawbacks known in the prior art.

The inventors have recognized that the dynamics of cells settling onto the functionalized wall surface, cells attaching to cells of the functionalized wall surface and cells detaching from the functionalized wall surface often is complex. The inventors found that during the incubation process, effector cells can move over the functionalized surface to find matching target cells. Additionally, effector cells may deform and/or visually disappear when they are close to or bind to target cells or the substrate. Moreover, during the force ramping also target cells and/or debris may detach from the functionalized wall surface.

The effector cells and the target cells however may be similar of size and/or shape, resulting in a very poor contrast between foreground and background, especially when the effector cells are very close to the target cells. This contrast problem can also arise even if there is a large difference in shape and size between the target and effector cells. The fact that during the imaging of the processes a very poor contrast between foreground and background may exist or that—close to the functionalized wall—effector cells simply disappear, i.e. are no longer visible in the images and thus cannot be tracked anymore, may introduce "false events" during the cell detection and tracking process. These false events may complicate the automated cell detection and tracking process. The embodiments in this application address this problem.

In an aspect, the invention may relate to a method for determining interaction between cells wherein the method may comprise determining or receiving a sequence of images representing manipulating first cells, in a holding space, the holding space including a functionalized wall comprising second cells, the manipulating including settling of the first cells onto the functionalized wall and applying a force on the settled first cells. The method may further comprise detecting groups of pixels representing first cells in first images representing the settling of the first cells onto the functionalized wall and tracking locations of detected first cells in the first images; and, determining settling events, a settling event being determined if a cell is no longer distinguishable from the background, the location in the image at which a cell settling event is detected defining a cell settling location. The method may also comprise detecting groups of pixels representing first cells in second images captured during the application of the force and tracking locations of detected first cells, wherein tracked locations of a detected first cell in the second images form a tracking path, the first location of the tracking path defining a pop-up event, the location in a second image at which a pop-up event is detected defining a pop-up location. The method may further comprise determining detachment events based on the settling locations and based on the pop-up locations, a detachment event defining a first cell being detached from a second cell due to application of the force on the first cell, and determining information about the interaction between first and second cells based on the force applied to the first cells.

Thus, images of a force spectroscopy experiment are analyzed for detecting settling events and pop-up events.

Herein, the term force spectroscopy is used to indicate any system or method in which a force is applied on particles of interest while a response of the particles to the force is monitored e.g. by imaging the particles with a microscope.

Settling events relate to events in the images wherein positions of groups of pixels representing first cells that are introduced into the holding space above the functionalized wall are detected and tracked until they are no longer trackable. These first cells become no longer trackable in the images because they move towards the functionalized wall, move over the wall and may bind to second cells or to the wall itself so that the visibility and/or contrast of the tracked cells drops below a certain level. At that level the groups of pixels in the images that are detected as first cells are no longer distinguishable or recognizable from the pixels representing the image background (i.e. the functionalized wall including the second cells). Similarly, pop-up events relate to events in the images wherein after the settling of the first cells on the functionalized wall surface (and thus are no longer visible or at least no longer clearly distinguishable or recognizable in the images) a force is applied to the first cells that are settled onto the functionalized wall and possibly bound to the second cells.

Thus, during the settling phase, positions of a first cell are tracked in a sequence of first images up to an image wherein tracking is no longer possible due to the fact that the first cell is no longer distinguishable from the background that image. The location where the cell disappears defines a settling event. While no longer being visible in subsequent images, the first cell may continue to move over the functionalized wall surface, until it attaches to a second cell of the functionalized wall surface. Hence, in that case the location of the settling event will not coincide with a pop-up event and a correlation scheme is needed in order to link the settling event with the pop-up event.

Application of a force that is directed away from the functionalized wall introduces a pulling force onto the first cells so that in a certain force range the first cells will detach from the second cells and move away from the functionalized wall. In the images, this process is visible as groups of pixels appearing (pop-up) in the images that are captured during the application of the force, which are detected as cells.

During the application of force, not only first cells can detach, but also debris and/or second cells, which—during the image processing—may be detected as cells. Furthermore, due to the force field in the holding space, cells may start moving and accumulate at certain positions. Correlating the positions at which settling events took place (during the settling process) with the positions at which a pop-up event took place (during the application of the force ramp) allows detection of "true" detachment events, i.e. events that relate to a first cell that is attached (bound) to a second cell and that becomes detached from the second cells because a certain pulling or pushing force is applied to the first cell. The invention thus allows accurate and robust detection of detachment events, which are needed to determine information about the interaction of the first cells with the second cells. False positives can be efficiently filtered out which is especially advantageous in case of examining substantial amounts of cells in the holding space.

The process is particular effective in case cells, e.g. effector cells and/or target cells, are not labeled with a fluorescent body (e.g. by attaching one or more chromophores/fluorophores to the cells).

In this application, the term cell should be interpreted to also include a cell of a pluricellular body, such as small clumped cell groups, plant or animal biopts, dividing cells, budding yeast cells, colonial protists, etc. A cell may also be a cell of an animal embryos in an early stage of development (e.g. the morula-stadium of a mammal, possibly a human embryo).

In an embodiment, the holding space may be configured as a microfluidic chip.

In an embodiment, the determining of the detachment events may include determining pairs of settling locations and pop-up locations and classifying the pairs as valid or invalid detachment events based on a distance between a settling location and a pop-up location, tracking paths, velocity of a cell at a pop-up location, or any other pixel-derived value or combination of values.

In an embodiment, the determining of the detachment events may include: determining a distance between a settling location and a pop-up location and determining a detachment event based on a threshold value. In an embodiment, a detachment event may be determined if the distance between a settling location and a pop-up location in the images is smaller than the threshold value. Hence, a distance parameter (e.g. measured in terms of pixels) may be used to correlate a settling event with a pop-up event. Only a pop-up event that appears in the images during the application of the force that is within a certain distance from the location of a settling event is determined as a detachment event. If multiple pop-up events are within this distance, distance and/or time may be used to determine which pop-up event is determined as a detachment event. For example, the pop-up event closest to the location of the settling event or the first pop-up event within the distance may be selected as a detachment event.

In an embodiment, the determining if is no longer distinguishable from the background may be based on at least one of: intensity values of pixels of the group of pixels representing a cell; a shape, texture and/or dimensions of the group of pixels representing a cell; and/or, a contrast ratio between pixel values of group of the pixels representing a cell and pixels values representing the background of an image in which the group of pixels is tracked. Hence, during tracking groups of pixels that are detected (recognized) as cells may be classified as trackable or not (or no longer) trackable based on properties of the group of pixels, e.g. intensity of the pixel values, shape or dimensions of the group of pixels, etc.

In an embodiment, the classification into a trackable or non-trackable cell may be based on changes in pixel values of a group of pixels representing a cell, preferably the changes including changes into intensity values, a shape, texture and/or, a contrast ratio between pixel values of group of the pixels representing a cell and pixels values representing the background of an image in which the group of pixels is tracked. In this embodiment, during tracking groups of pixels that are detected (recognized) as cells may be classified as trackable or not (or no longer) trackable based on changes in the properties of the group of pixels over time.

In an embodiment, the determining of the images may include: determining or receiving one or more background images of the functionalized wall comprising the second cells; using the one or more background images to remove the background from the images representing the manipulation of the first cells. The removal of the background (i.e. pixels representing parts of the functionalized wall) may improve the detection and tracking and the determination of settling events and pop-up events.

In an embodiment, the determining of detachment events may include: determining or receiving locations of one or more non-functional areas in the images of the functionalized wall surface, a non-functional area defining an area in the functionalized wall surface in which the second cells are absent; disregarding a pop-up location in the determining of detachment events if a pop-up location is located in or within a predetermined distance from the one or more non-functional areas. In this embodiment, the structure of the functionalized wall surface may be taken into account when determining detachment events. For example, in certain situations, parts of the functionalized wall surface may include parts where no second cells are attached to the wall. This information may be taken into account in the determination of detachment events.

In an embodiment, the determining of detachment events may include: determining or receiving one or more cluster locations in the images captured during the application of the force, a cluster defining an aggregation of cells which are not bound to the functionalized cell surface in the images when a force is applied to the first cells; disregarding a pop-up location in the determining of detachment events if a pop-up location is detected within one of the one or more cluster locations or if a pop-up location is detected within a predetermined distance of one of the one or more cluster locations.

In an embodiment, the determining of detachment events may include: disregarding a pop-up location in the determining of detachment events if the pop-up location is located within a predetermined distance of the edges of the images. Due to applied force, unbound cells originating from areas in the holding space that are outside the field of view of the imaging system may move into the field of view of the imager. These unbound cells may be detected as a pop-up event which can be disregarded in the determination of detachment events.

In an embodiment, the tracking a location of a detected cell may include: linking positions of detected cells in subsequent images using a minimization technique, preferably a global minimization technique.

In an embodiment, the method may further include: determining an avidity curve based on the detachment events and the force associated with each of the detachment events.

In an embodiment, the first cells may be (or may comprise) effector cells and the second cells are (or may comprise) target cells.

In another embodiment, the second cells are (or may comprise) effector cells and the first cells are (or may comprise) target cells. Hence, in certain embodiments, the second cells may be effector cells and the first cells may be target cells. For example, effector cells may be substantially smaller than the target cells. In such situation, it may be advantageous to prepare a functionalized wall surface comprising effector cells and to flush target cells into the flow cell and allow the target cells to incubate with the effector cells. Hence, in this case the assay may be inverted. i.e. the surface of the functionalized wall is coated with effector cells and the detachment forces are measured by pushing the target cells of the effector cell layer.

In an embodiment, second cells may include 'dead' target cells, e.g. cells of an autopsy (autopsy material) or the like.

In an embodiment, the first cells and/or second cells may include at least one of: lymphocytes, monocytic cells, granulocytes, T cells, natural killer cells, B-Cells, CAR-T cells, dendritic cells, Jurkat cells, bacterial cells, red blood cells, macrophages, TCR Tg T-cells, OT-I/OT-II cells, splenocytes, thymocytes, BM derived hematopoietic stem cells, TILs, tissue derived macrophages, innate lymphoid cells.

In another embodiment, the first and/or second cells may include at least one of: tumor cells, stem cells, epithelial cells, B16 melanoma, fibroblasts, endothelial cells, HEK293, HeLa, 3T3, MEFs, HuVECs, microglia, neuronal cells.

Thus, depending on the type of experiment, different cell types may be used for the first cells, i.e. the unbound cells that are introduced (flushed) into the holding space and for the second cells, i.e. the cells that are attached to (or part of) the functionalized wall. In further embodiment, the first cells and/or second cells may comprise combinations of target and effector cells (where one of the functions of effector cells is to recognize specific target cells). Additionally, and/or alternatively, the first cells and/or second cells may include cells which are not classified as target or effector cells.

In an embodiment, the force applied to the first cells is an acoustic force. In another embodiment, the force applied to the first cells is an inertial force, e.g. a centrifugal force. In an embodiment, the force applied to the first cells is increased as a function of time.

In an embodiment, applying a force to the first cells include: generating a resonant bulk acoustic wave in the holding space, the resonant bulk acoustic wave exerting an acoustic force on each of the first cells in a direction away from the surface of the holding space.

In an embodiment, the imaging system has a focal plane essentially parallel to the functionalized wall surface.

In an aspect, the invention may relate to a module for analyzing images of cells being manipulated in a holding space, the module comprising a computer readable storage medium having computer readable program code embodied therewith, and a processor, preferably a microprocessor, coupled to the computer readable storage medium, wherein responsive to executing the computer readable program code, the processor is configured to perform executable operations comprising: determining or receiving a sequence of images representing manipulating first cells, in a holding space, the holding space including a functionalized wall comprising second cells, the manipulating including settling of the first cells onto the functionalized wall and applying a force on the settled first cells; detecting groups of pixels representing first cells in first images representing the settling of the first cells onto the functionalized wall; tracking locations of detected first cells in the first images, wherein for each image during tracking cells are classified as being trackable or not trackable; and, determining settling events, a settling event being determined if during tracking a tracked cell is classified as non-trackable, the location in the image at which a cell settling event is detected defining a cell settling location; detecting groups of pixels representing cells in second images captured during the application of the force and tracking locations of detected cells, wherein tracked locations of a detected cell in the second images form a tracking path, the first location of the tracking path defining a pop-up event, the location in a second image at which a pop-up event is detected defining a pop-up location; and, determining detachment events based on the settling locations and based on the pop-up locations, a detachment event defining a first cell being detached from a second cell due to application of the force on the first cell, and determining information about the interaction between first and second cells based on the force applied to the first cells.

The module described above may be configured to execute any of the method steps described in this application.

In yet another aspect, the invention may relate to a system for determining interaction between cells comprising: a sample holder comprising a holding space for cells; a force generator for applying a force to the cells; an imaging system capturing images of the cells in the holding space; a controller module for controlling the force generator and the imaging system; a computer readable storage medium having computer readable program code embodied therewith, and a processor, preferably a microprocessor, coupled to the computer readable storage medium, wherein responsive to executing the computer readable program code, the processor is configured to perform executable operations comprising: determining or receiving a sequence of images representing manipulating first cells, in a holding space, the holding space including a functionalized wall comprising second cells, the manipulating including settling of the first cells onto the functionalized wall and applying a force on the settled first cells; detecting groups of pixels representing first cells in first images representing the settling of the first cells onto the functionalized wall; tracking locations of detected first cells in the first images, wherein for each image during tracking cells are classified as being trackable or not trackable; and, determining settling events, a settling event being determined if during tracking a tracked cell is classified as non-trackable, the location in the image at which a cell settling event is detected defining a cell settling location; detecting groups of pixels representing cells in second images captured during the application of the force and tracking locations of detected cells, wherein tracked locations of a detected cell in the second images form a tracking path, the first location of the tracking path defining a pop-up event, the location in a second image at which a pop-up event is detected defining a pop-up location; and, determining detachment events based on the settling locations and based on the pop-up locations, a detachment event defining a first cell being detached from a second cell due to application of the force on the first cell, and determining information about the interaction between first and second cells based on the force applied to the first cells.

The system described above may be configured to execute any of the method steps described in this application.

The invention may also relate to a computer program or suite of computer programs comprising at least one software code portion or a computer program product storing at least one software code portion, the software code portion, when run on a computer system, being configured for executing any of the method steps described above.

The invention may further relate to a non-transitory computer-readable storage medium storing at least one software code portion, the software code portion, when executed or processed by a computer, is configured to perform any of the method steps as described above.

The invention will be further illustrated with reference to the attached drawings, which schematically will show embodiments according to the invention. It will be understood that the invention is not in any way restricted to these specific embodiments.

BRIEF DESCRIPTION OF THE DRAWINGS

FIG. 1 depicts a schematic of a force spectroscopy system according to an embodiment of the invention;

FIGS. 2A and 2B schematically depict a flow cell for a force spectroscopy system according to an embodiment of the invention;

FIG. 5A-5E depicts a schematic of a cell selection, tracking and classification process according to an embodiment of the invention;

DETAILED DESCRIPTION

Figure 2B:
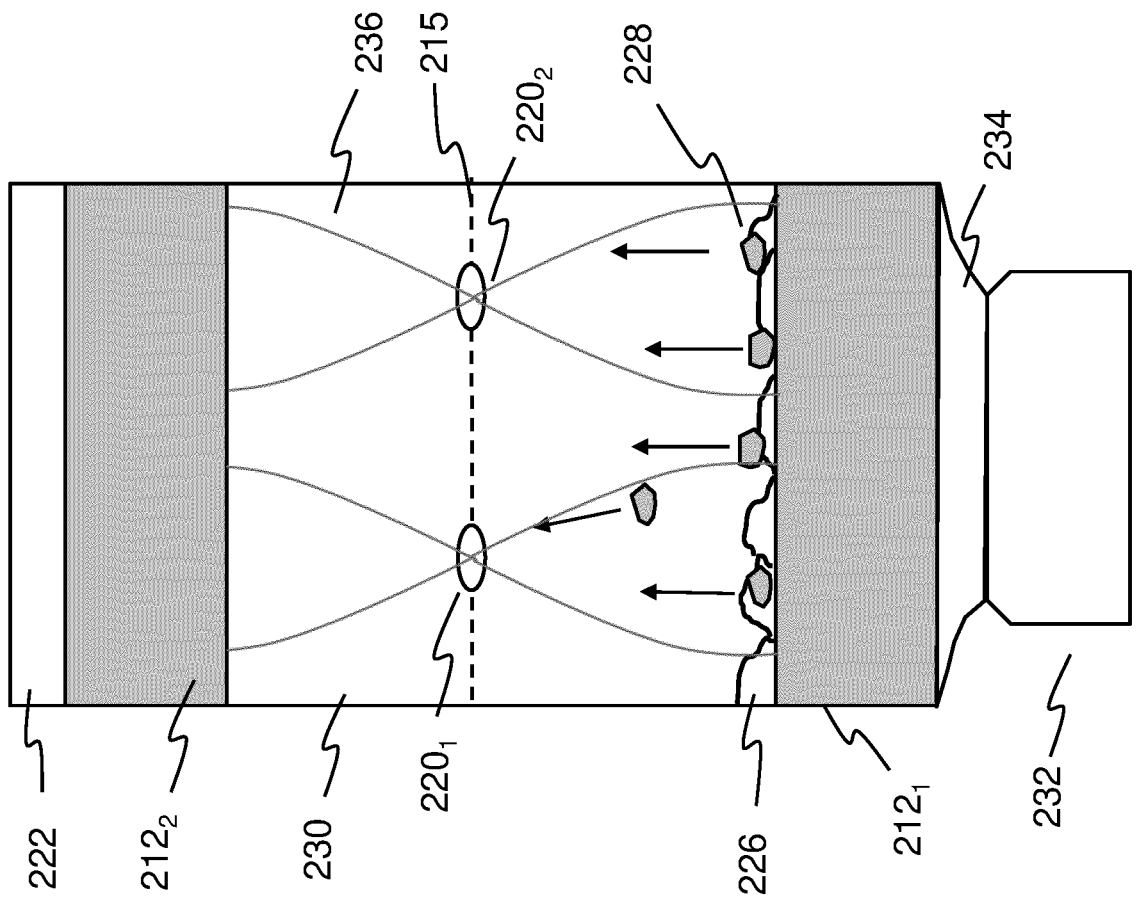

FIG. 1 schematically depicts a force spectroscopy system according to an embodiment of the invention. The force spectroscopy system 100 may comprise a sample holder 102 comprising a holding space 104 for holding a sample 106 for holding cellular bodies in a fluid medium, e.g. a liquid or a gel. The holding space may be part of a flow cell (also referred to as a microfluidic cell). The system may further comprise a force field generator 108, e.g. an acoustic wave generator based on a piezo element, connected to the sample holder 102 for generating a bulk acoustic wave in the holding space so that a force is exerted on cellular bodies that may be present in the holding space. The force field generator may be connected to a controller 110 so that the force exerted on the cellular bodies can be controlled.

The system of FIG. 1 may further comprise an imaging system for imaging the processes in the holding space. The imaging system may include a microscope 112 including optics, e.g. adjustable objective 114, and a camera 116 for capturing pictures, e.g. video frames, of the processes in the holding space. The imaging system may be connected to a computer 118 comprising a processor connected a memory comprising one or more software programs, which when executed, allow control of the different elements of the system.

The system may further comprise a light source 120 for illuminating the sample using any suitable optics (not shown) to provide a desired illumination intensity and intensity pattern, e.g. plane wave illumination, Köhler illumination, etc., known per se. Here, the light 122 emitted from the light source may be directed through the force field generator 108 to (the sample in) the sample holder 102 and sample light 124 from the sample is transmitted through the objective 114 and through an optional tube lens 126 and/or further optics (not shown) to the camera 116. The objective and the camera may be integrated. In an embodiment, two or more optical detection tools, e.g. with different magnifications, may be used simultaneously for detection of sample light, e.g. using a beam splitter.

In another embodiment, not shown but discussed in detail in WO2014/200341, the system may comprise a partially reflective reflector and light emitted from the light source is directed via the reflector through the objective and through the sample, and light from the sample is reflected back into the objective, passing through the partially reflective reflector and directed into a camera via optional intervening optics. Further embodiments may be apparent to the reader.

The sample light may comprise light affected by the sample (e.g. scattered and/or absorbed) and/or light emitted by one or more portions of the sample itself e.g. by chromophores/fluorophores attached to the cellular bodies.

Some optical elements in the system may be at least one of partly reflective, dichroic (having a wavelength specific reflectivity, e.g. having a high reflectivity for one wavelength and high transmissivity for another wavelength), polarisation selective and otherwise suitable for the shown setup. Further optical elements e.g. lenses, prisms, polarizers, diaphragms, reflectors etc. may be provided, e.g. to configure the system 100 for specific types of microscopy.

The sample holder 102 may be formed by a single piece of material with a channel inside, e.g. glass, injection moulded polymer, etc. (not shown) or by fixing different layers of suitable materials together more or less permanently, e.g. by welding, glass bond, gluing, taping, clamping, etc., such that a holding space 106 is formed in which the fluid sample is contained, at least during the duration of an experiment. While, the force spectrometry system of FIG. 1 includes an acoustic force generator, other ways of applying a force on the cells may be used as well. For example, a force spectrometry system that uses a centrifugal force generator for applying a force on the cells is described in more detail with reference to FIG. 12.

FIGS. 2A and 2B schematically depict cross-sectional views of a flow cell for a force spectroscopy system according to an embodiment of the invention. The sample holder 212 may comprise a first base part $206_1$ that has a recess being, at least locally, U-shaped in cross section and a cover part $206_2$ to cover and close (the recess in) the U-shaped part providing an enclosed holding space in cross section.

Further, the sample holder 212 may be connected to a fluid flow system 214 for introducing fluid and unbound cells into the holding space of the sample holder and/or removing fluid from the holding space, e.g. for flowing fluid through the holding space (see arrows in FIG. 2A depicting the flow direction). The fluid flow system may be comprised in or part of a manipulation and/or control system including one or more of reservoirs 216, pumps, valves, and conduits 218,219 for introducing and/or removing one or more fluids, sequentially and/or simultaneously. The sample holder and the fluid flow system may include connectors, which may be arranged on any suitable location on the sample holder, for coupling/decoupling. The sample holder may further include a force field generator 222, e.g. an acoustic wave generator which may be implemented based on a (at least partially transparent) piezoelectric element connected to a controller 224.

FIG. 2B schematically depicts a cross-section of part of the sample holder including objective 232 that is positioned underneath part of a sample holder (a chip) wherein the sample holder may comprise a capping layer $212_1$, a matching layer $212_2$, a fluid medium 230 contained in the holding space formed by the capping and the matching layer, and part of a force generator 222, e.g. a piezo element. An immersion liquid 234 between the objective and the capping layer may be used to improve the optical numerical aperture (NA) of the imaging system but the data shown in FIGS. 6 and 7 was obtained using an embodiment without immersion liquid. Application of an AC voltage to the piezo element at an appropriate frequency will generate a resonant bulk acoustic standing wave 236 in the sample holder. The standing wave may have a nodal plane 215 in the fluid layer at a certain height above the functionalized wall comprising target cells 226 attached to the wall of the sample holder and effector cells 228 that are bound to the target cells. The standing wave may also have lateral nodes $220_{1,2}$. Cells that have a positive acoustic contrast factor with respect to the fluid medium will experience a force towards to the nodes.

One or more software programs that run on the computer 118 of the force spectroscopy system may be configured to control the camera, the force field generator and the flow cell to conduct different experiments. In a typical experiment, cells, e.g. effector cells, may be flushed into the holding space of the flow cell and may interact, e.g. bind, with the target cells. This interaction can be probed by analysing the response of cells that are bound to target cells as a function of the force applied. Typically, the response of the cells is determined by analysing video frames that are captured by the camera. To that end, the computer may include an image processing module 128 comprising one or more image processing algorithms for analysing the response of the cells when they are manipulated in the flow cell using the force field generator. The image analysis of the video frames is described hereunder in greater detail.

FIG. 3A-3D depict schematics of manipulating cells in a holding space of a microfluidic cell comprising a functionalised wall surface to which target cells are attached. The microfluidic cell may be part of a force spectroscopy system as described with reference to FIGS. 1 and 2. The manipulation of the cells may be imaged from below or from the top using an imaging system as described with reference to FIG. 1. As depicted in FIG. 3A, the process may start with flushing cells 306, e.g. effector cells, into the holding space of the microfluidic chip, comprising a functionalized wall 302 including target cells 304. The introduction of the cells into the holding space may take a predetermined period of time, e.g. between 1 and 5 seconds. After flushing, the cells are allowed to settle onto the functionalized wall comprising the target cells (FIG. 3B). When the effector cells reach the functionalized wall, the cells may move around over the functionalized surface until they find a suitable target cell to bind to (surveillance) thus forming a bound effector—target cell pair 310 (FIG. 3C). The steps of effector cells settling onto the functionalized wall and binding to target cells may be referred to as the incubation phase. In a typical experiment, incubation may take up to 1-15 minutes or longer.

As will be described hereunder in more detail, the incubation phase may be imaged and when the cells are introduced into the holding space and move towards the functionalized wall, groups of pixels in the captured images may be detected and tracked. However, as effector cells approach the functionalized wall, move other the wall surface and bind to target cells, the contrast between pixels representing effector cells and pixels representing the functionalized wall including the target cells may become very low so that if the contrast drops below a certain level cells can no longer be reliably detected and tracked.

After the incubation phase, a force may be applied to the effector cells that are bound to the target cells. The force may have a direction away from the functionalized wall surface. Typically, a force ramp will be applied to the effector cells, so that if the force becomes larger than the binding force, effector cells will detach from the target cells and move away in the direction of the force (FIG. 3D). As the target cells are bound firmly to the functionalized wall, the force will "pull" the effector cells from the target cells and move the effector cells away from the functionalized wall surface. Pulling or pushing the effector cells from the target cells will be visible in the images as groups of pixels representing cells that "pop up" in the foreground against a background image of the functionalized wall. Such an event may be referred to as a pop-up event.

When the force is larger than the binding force, the effector cell will detach from the target cell and move in a direction that depends on the applied force, which may have a component perpendicular to the functionalized wall (e.g. the z-direction) and two components in the plane of the functionalized wall (e.g. the x and y direction). The location in the image in which a pop-up event is detected (i.e. the contrast between groups of pixels representing cell and pixels representing the background is above a certain level) and the point in time at which the pop-up event occurred can be determined on the basis of the images (video frames) which are captured during the experiment. The time at which cells detach may determine the force that is exerted on the effector cells. In a typical experiment, the force ramp may take between 2-10 minutes, but it can also be shorter or longer.

Based on a measurement scheme as described with reference to FIG. 3, various parameters of the effector cells can be determined. For example, FIG. 4 depicts two cell avidity curves which may be determined by applying a force ramp to the functionalized wall surface and determining the number of attached cells as a function of the applied force. Based on the type of effector and target cells, cells may exhibit a low cell avidity curve 402 (weak binding forces between effector and target cells) or a high cell avidity curve 404 (strong binding forces between effector and target cells).

Figure 3:
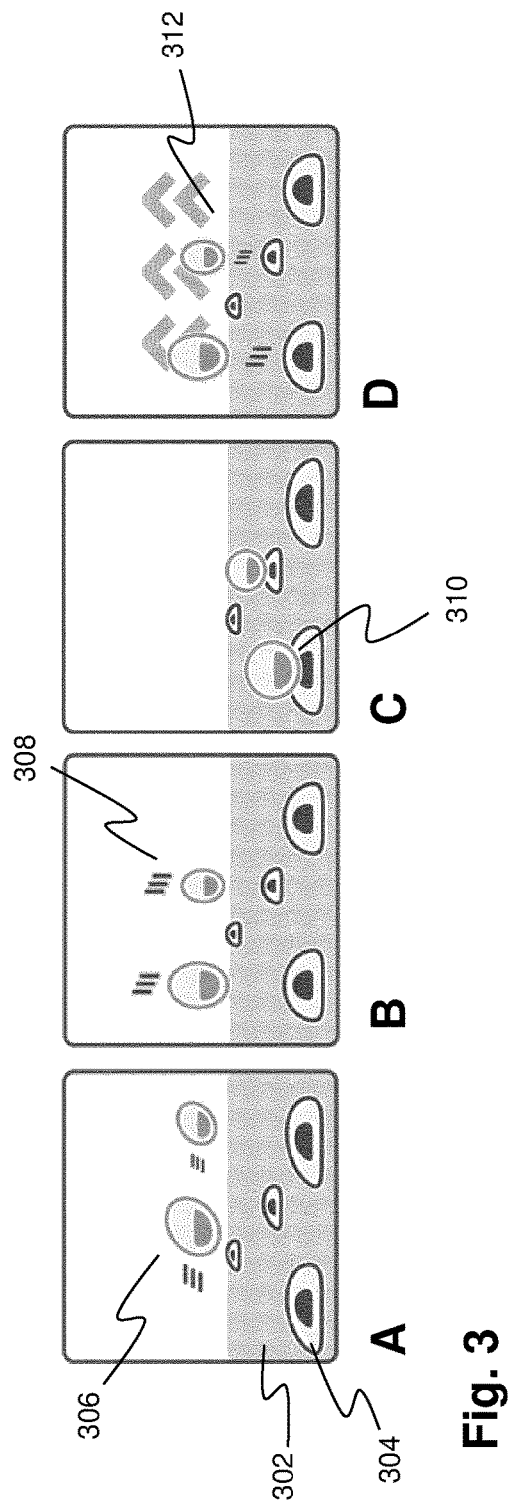
FIG. 3 depicts a schematic of a typical experiment in a force spectroscopy system according to an embodiment of the invention.
Figure 4:
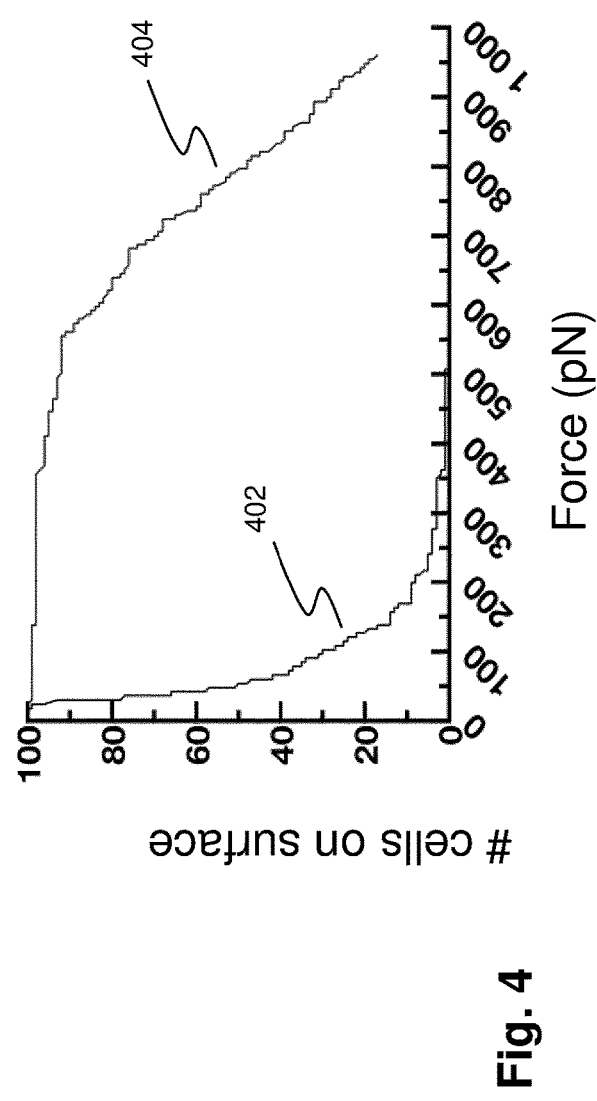
FIG. 4 depicts two cell avidity curves determined using a force spectroscopy system according to an embodiment of the invention.

While FIGS. 2A,2B and 3 describe experiments wherein unbound effector cells are introduced in the holding space and target cells are attached to the functionalized wall other configuration are also possible. For example, in certain embodiments, unbound target cells may be introduced into the holding space, while effector cells are attached to the functionalized wall.

FIG. 5A-5E depict schematics of images of cells in a microfluidic cell which are manipulated using a force spectroscopy system. These images are processed based on an image processing algorithm according to an embodiment of the invention. As already described with reference to FIG. 1, the force spectroscopy system comprises an imaging system, e.g. a video camera, for capturing images of the process in the microfluidic cell. Depending on the system configuration, the images may represent a top view or bottom view of the functionalized wall comprising the target cells. During a typical force spectroscopy experiment, many video frames of processes in the flow cell will be captured. The images of FIG. 5A-5E are schematics of representative images of the flow cell during the different phases of a force spectroscopy experiment as e.g. described with reference to FIG. 3. The images of a force spectroscopy experiment may be associated with a time of a clock, e.g. time-stamped, so that information derivable from the images can be determined as a function of time and the force corresponding to the time-stamps may be correlated with the images.

FIG. 5A depicts an image 502 representing a top view of the microfluidic cell including a functionalized wall 503 comprising target cells 504. This image may represent an exemplary situation at a start of a force spectroscopy experiment, wherein unbound, unlabelled cells are flushed into the microfluidic cell. The cells are visible in the image against a background representing the functionalized wall comprising the target cells. Known image processing algorithms may be used to detect and locate effector cells in each image and to track the locations of the detected cells in subsequent images. Such image processing algorithm may for example detect groups of pixels of a certain intensity and use classification rules that include e.g. size, geometry, contrast and changes in size, geometry and contrast, to determine if such group of pixels that is detected in subsequent images may be classified as a trackable cell.

A dotted circle 505 in the image may indicate that the algorithm has detected a group of pixels 506 within the circular area which is classified as a trackable cell. The cells that are visible in the images are depicted using a white color. This detection and classification process may be applied to the captured images. The location of detected groups of pixels that are classified as trackable, unbound cells (which may move both parallel and perpendicular to the functionalized wall) may be determined so that the movement of the detected cell as a function of time can determined. The locations of a cell that is detected and tracked may form a so-called tracking path (not shown). Each cell that is detected and tracked in subsequent images may be linked with a unique identifier so that the locations of a tracked cell (the tracking path) and other information can be stored on a storage medium of the computer that executes the image processing algorithm.

During the incubation phase, effector cells that are introduced into the microfluidic cell will gradually descent by e.g. gravitational forces towards the functionalized wall. Further, the cells may move over the surface of the functionalized wall until they encounter suitable target cells to bind to. When cells are descending towards the functionalized wall, the change in contrast, shape and/or dimensions of the group of pixels representing a cell may cause the image processing algorithm to classify the group of pixels as no longer trackable. Thus, during the incubation phase, the classification of a group of pixels that is classified as a trackable cell may change into non-trackable (i.e. a cell in a first image is no longer distinguishable from background of the first image) when it moves towards the wall surface and binds to a target cell. Detected and tracked groups of pixels that are classified as cells may "disappear" into the background of pixels representing the functionalized wall surface. In FIG. 5B non-trackable cells $508_{1\text{-}3}$ that are settled onto the wall surface have a grey color.

During the tracking of detected cells in subsequent images, the image processing algorithm may determine a so-called cell settling event in an image if the classification of a group of pixels is changed from a trackable cell into a non-trackable cell. The settling event may occur at a location in the image as schematically depicted in FIG. 5B by dotted squares $510_{1\text{-}3}$. The location in the image at which a cell settling event is determined defines a cell settling location.

Figure 5D:
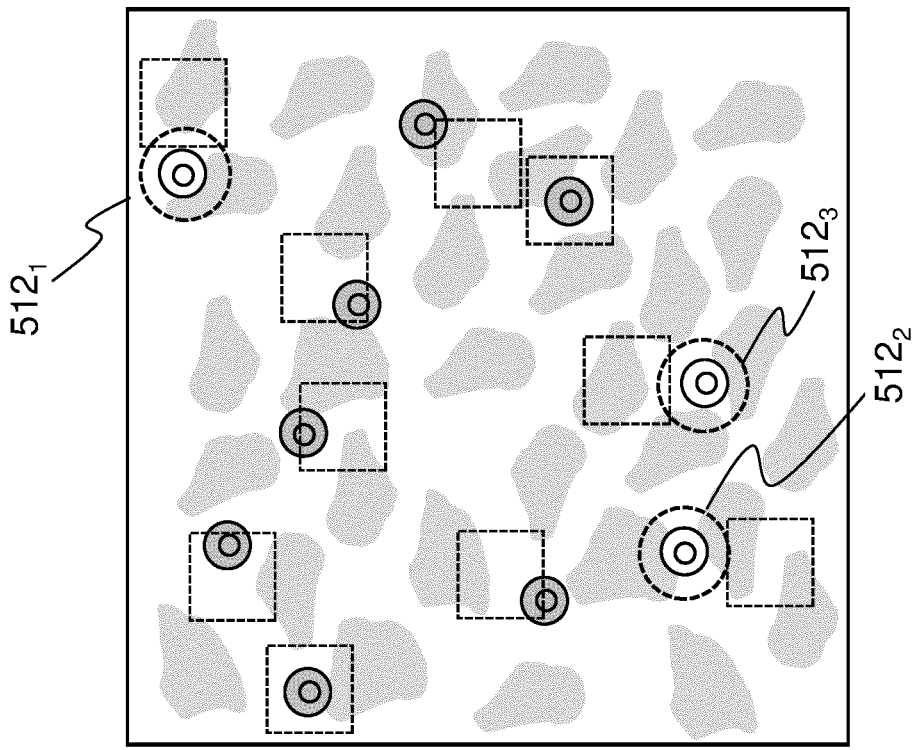
Figure 5C:
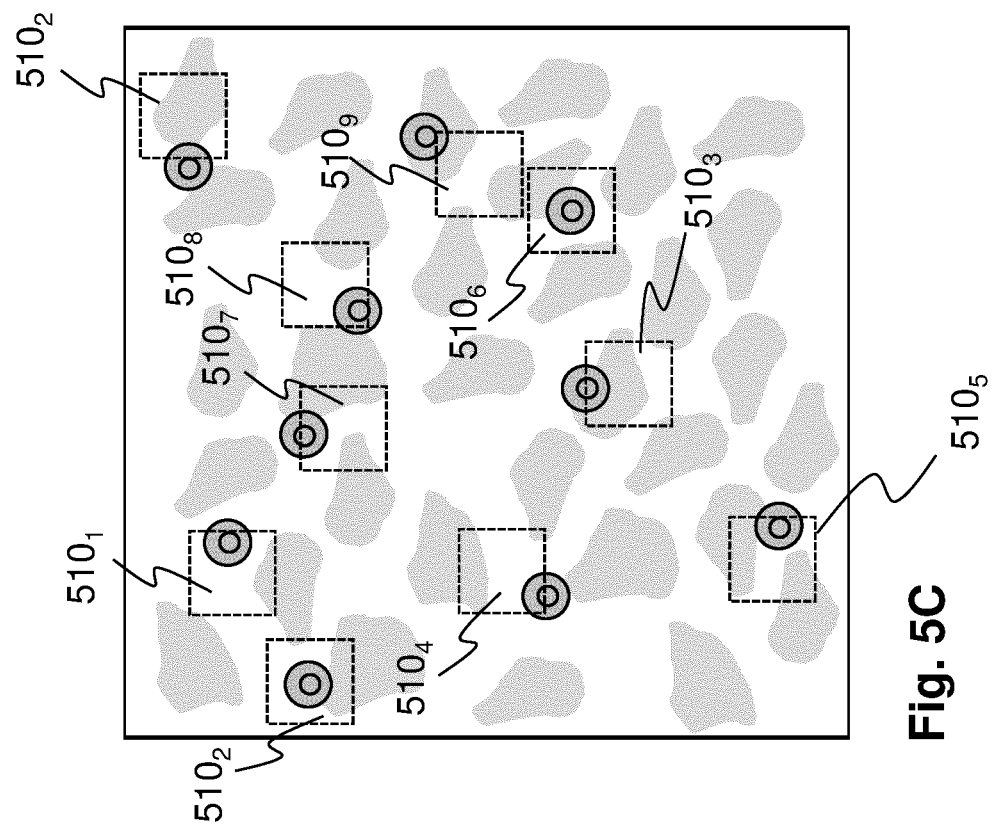

A cell settling event may further be associated with a time instance indicating at which time (or in which image of the video) the cell settling event was determined. Such time instance may for example be determined based on a clock or a time stamp of the image in which the event was detected. As shown in FIG. 5B, the location of a cell settling event $510_{1\text{-}3}$ may deviate from the actual location at which the cells $508_{1\text{-}3}$ bind to target cells. These actual locations cannot be determined by the algorithm as effector cells are no longer trackable if they are very close to the functionalized wall (the bound cells $508_{1-3}$ are gray colored and are therefore not visible in the image or at least will very difficult to detect in the image). The process of incubation may continue until for each (or most of) the cells a cell settling event $510_{1-9}$ is determined so that that (most of) the cells may be bound to target cells or the functionalized wall as depicted in FIG. 5C. In that case, the contrast between groups of pixels representing cells and pixels representing the background (the functionalized wall) may be below a certain level so that the algorithm may classify the cells as no longer trackable. The settling locations of the settled cells may be stored in a memory of a computer that executes the image processing algorithm.

Thereafter, a force generator of the force spectroscopy system, e.g. an acoustic force generator as explained with reference to FIGS. 1 and 2, may be switched on and images may be captured when a force is applied onto the cells that are bound to the target cells. FIG. 5D depicts an image illustrating this situation. The direction of the force generated by the force generator is pointing away from the functionalized wall surface. Hence, when a certain force is applied, cells may detach from the target cells and move away from the functionalized wall. Typically, the force may be increased as a function of time.

As shown in FIG. 5D, due to the exerted force, certain cells may detach which may become visible in the image as groups of pixels which the algorithm detects as cells $512_{1-3}$. Thus, groups of pixels classified as cells may "pop-up" out of the background formed by pixels representing the functionalized wall. Cells appearing in the image during the force ramp may be detected by the image processing algorithm in a similar way as described with reference to FIG. 5A. Groups of pixels that are detected by the image processing algorithm as cells are depicted by the dotted circles $512_{1-3}$ in FIG. 5D.

Further, the location at which a cell is detected (for the first time) as a cell may define a cell pop-up location. The location of detected cells in subsequent images may be tracked, wherein the tracked cells may not only move away from the functionalized wall but also sideward within the plane of the functionalized wall. For example, as illustrated in FIG. 2B, a bulk acoustic standing wave in the microfluidic cell may create an axial nodal plane substantially parallel to the functionalized wall. The axial nodal plane may be positioned at a certain height above the functionalized wall surface. Also, lateral acoustic nodes may develop in the holding space, which will cause lateral perturbations of the axial nodal plane. So, when cells detach from the functionalized wall, the unbound cells may move towards the nodal plane which is substantially parallel to the functionalized wall surface. Simultaneously they may move also laterally to settle in the superposition of the axial and lateral acoustic nodes.

Figure 5E:
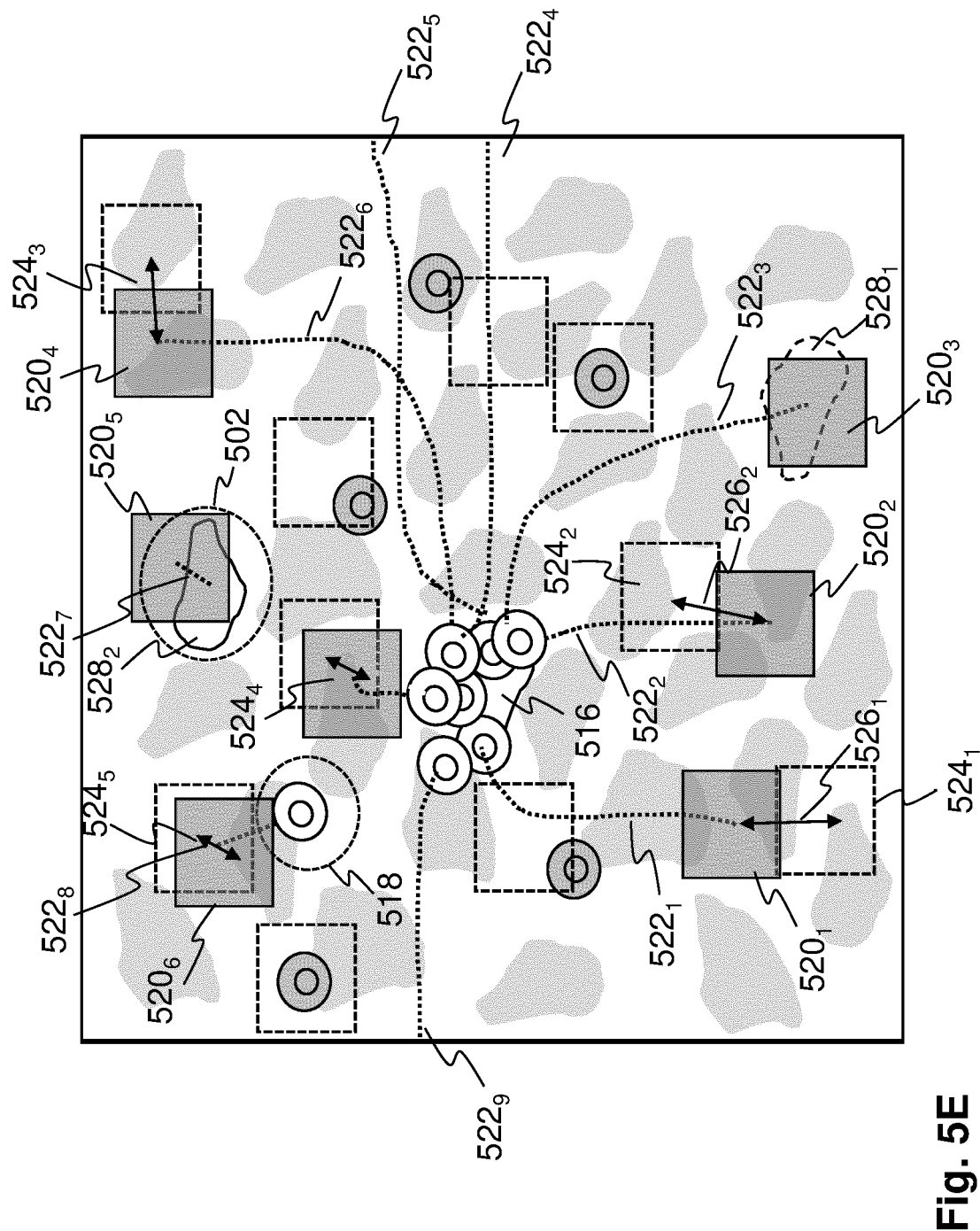

FIG. 5E depicts an image at a time instance when the force has increased over a period of time. As shown in this figure, groups of pixels that were classified as trackable cells in FIG. 5D moved towards a node of the force field. These tracked cells and other detected cells may form a cluster of cells 516 that are kept in position at the node. As shown in the figure, some unbound, detected cells, for example cell 518, move towards the cluster. Based on the locations of tracked cells in subsequent images, the image processing algorithm may determine tracking paths $522_{1-9}$ for each detected cell. In FIG. 5E tracking paths are represented by dotted lines. A tracking path represents the path along which a group of pixels which is classified as a trackable cell has moved to the cluster area. The image processing algorithm may determine the start of a tracking path as a pop-up event, i.e. a position in an image in which—during the force exertion—a group of pixels was detected for the first time. The position of the start of a tracking path may be referred to as a pop-up location. Pop-up events in the image of FIG. 5E are marked by the grey color squares $520_{1-7}$.

The tracking paths, the pop-up events and settling events may be used by the image processing algorithm to distinguish detachment events, i.e. pop-up events associated with detachment of a cell that was bound to a target cell, from other events, i.e. pop-up events that were recognized by the image processing algorithm but relate to other processes. As shown in FIG. 5E such "false positives" may include for example target cells $528_{1,2}$ that were detached during the force ramp up and detected and tracked as effector cells associated with a pop-up location $520_{3,5}$. The image processing algorithm may also classify a group of pixels representing such target cell as a trackable cell. Such false positives may be especially relevant in case the distinction (in terms of shape, dimensions, color, etc.) between effector cells and target cells is small.

Further, detached cells or debris that enter the field of view of the imaging system may be detected, classified as trackable cells and tracked until the cells accumulate at the cluster area. For example, tracking paths $522_{4,5,9}$ relate to detected cells or detected debris that is recognized by the algorithm as a cell. Such cells may come from an area outside the field of view and enter the field of view when the acoustic force attracts these cells to move towards the node. Events such as detached target cells or cells or debris that enter the field of view may be filtered out (disregarded) by using a distance correlation between the settling and pop-up events. This correlation is based on the observation that settled cells may move a certain limited distance before it finds a suitable target cell to bind to. Thus, the location of a settling event and a pop-up event of a detached cell (a detachment event) should be within a certain distance. When using the distance correlation to filter out the relevant pop-up events, the image processing algorithm may determine five detachment events $524_{1-5}$ in FIG. 5E.

Figure 6:
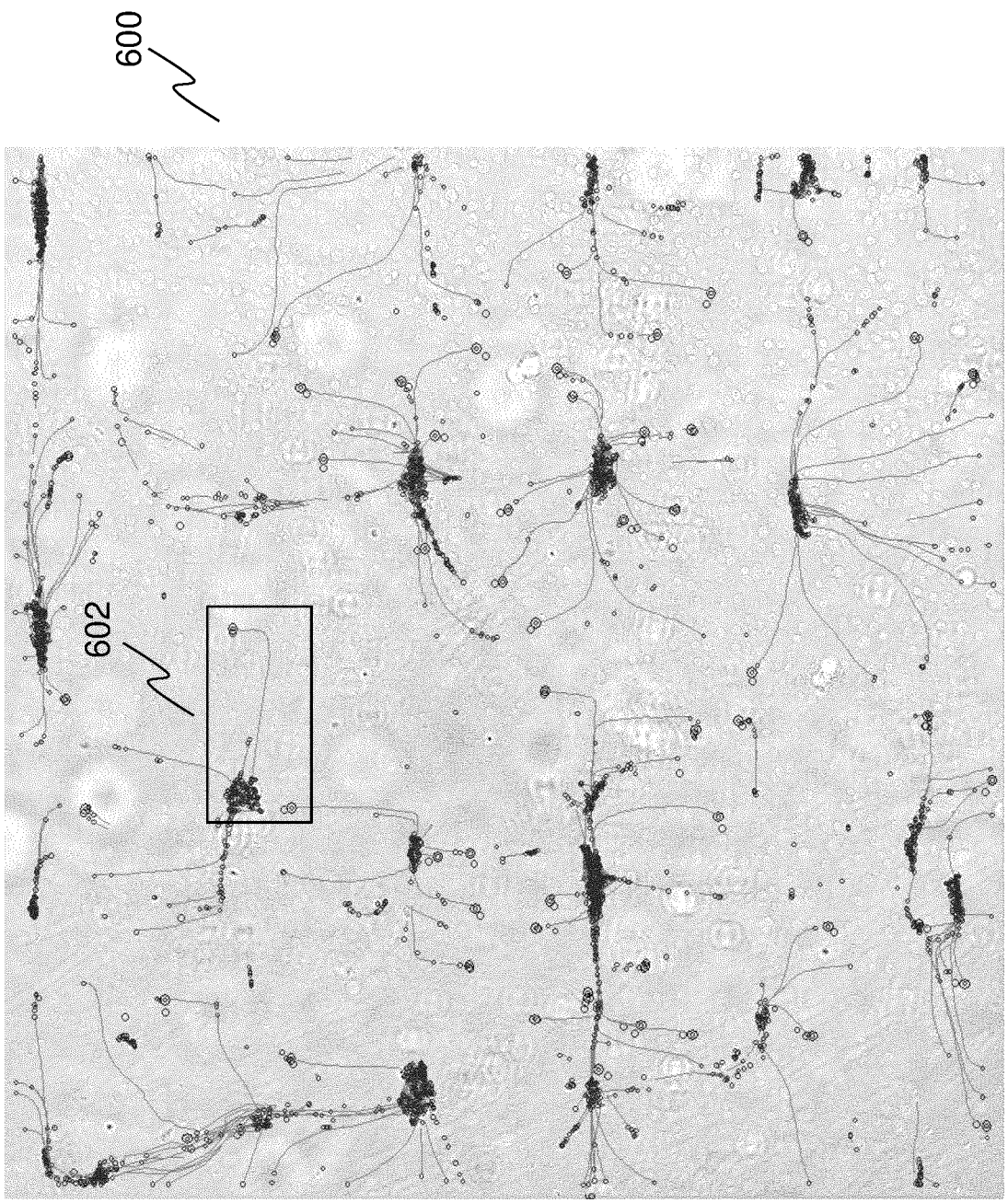
FIG. 6 depicts a video image of cells which is analyzed using an image processing algorithm according to an embodiment of the invention.
Figure 7:
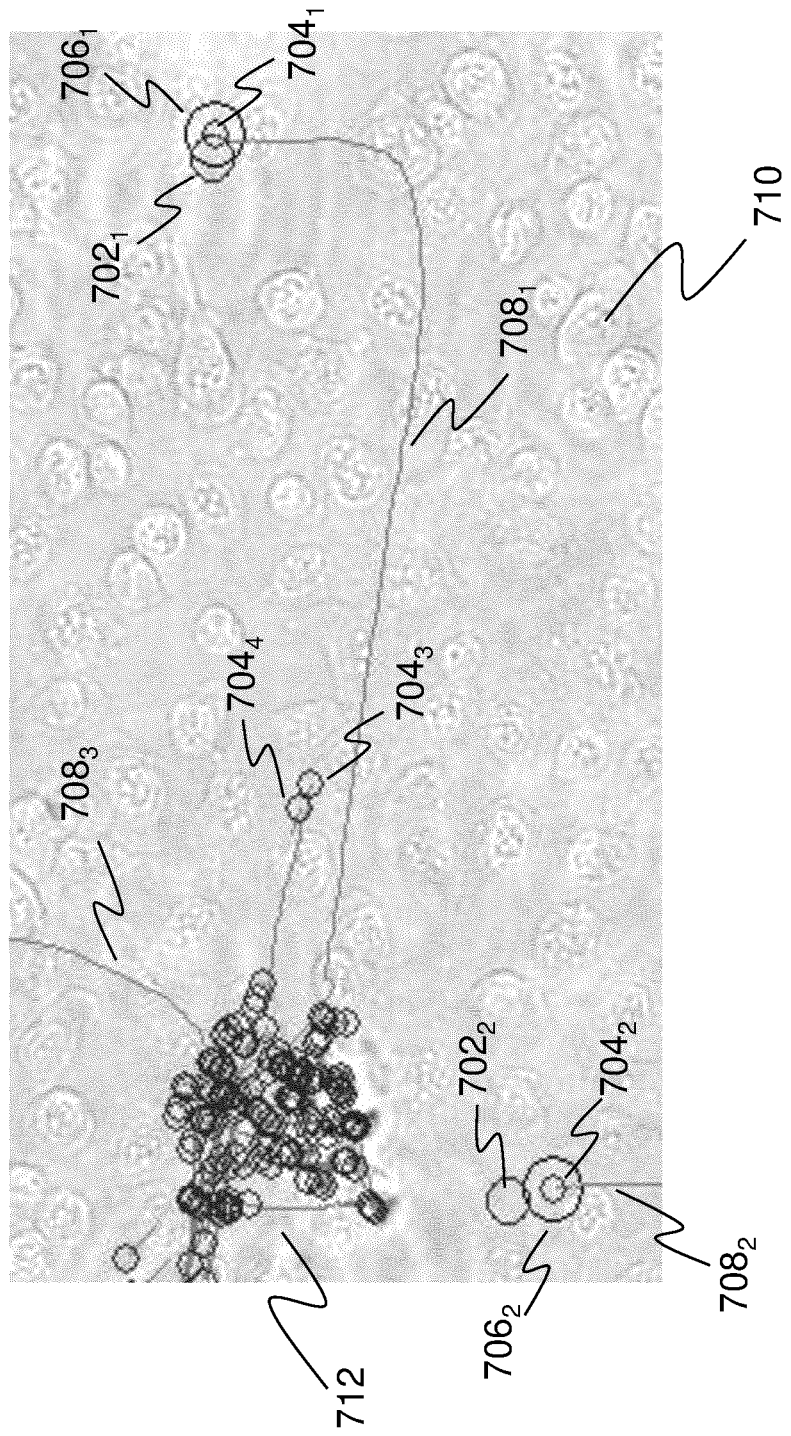
FIG. 7 depicts a video image of cells which is analyzed using an image processing algorithm according to an embodiment of the invention.

FIG. 6 depicts a video image taken by a camera of a force spectroscopy system which is analyzed using an image processing algorithm according to an embodiment of the invention. As shown in this video image 600, events and tracking paths are identified in the video image. The tracking paths are determined by tracking detected cells in multiple images. The paths show that cells are accumulated in positions of acoustic nodes that exists when the force generator of the AFS is turned on. FIG. 7 is an expanded picture of the area 602 of the video image of FIG. 6. FIG. 7 depicts a background of the functionalized wall including target cells 710, settling events $702_{1,2}$, pop-up events $704_{1-4}$ and tracking paths $708_{1-4}$ of detected cells during the force ramp that were accumulated in a cluster of cells 712 at an acoustic node. Correlating the settling events with the pop-up events allows identification of pop-up events associated with cells that were bound to a target cell. For example, a rule may be used that a pop-up event should be located within a predetermined distance from a settling event (but a more general classification for detachment events using other or more information than the location of settling and pop-up events may also be used). This distance may for example be expressed in a number of pixels or another suitable unit. Hence, pop-up events $704_{1,2}$ were marked as detachment events $706_{1,2}$ related to the detachment of an effector cell that was bound to a target cell. The parameters of these events, e.g. the force that was applied at the moment a detachment event was imaged, may be used for determining the interaction, e.g. the cell avidity or the like.

Figure 8:
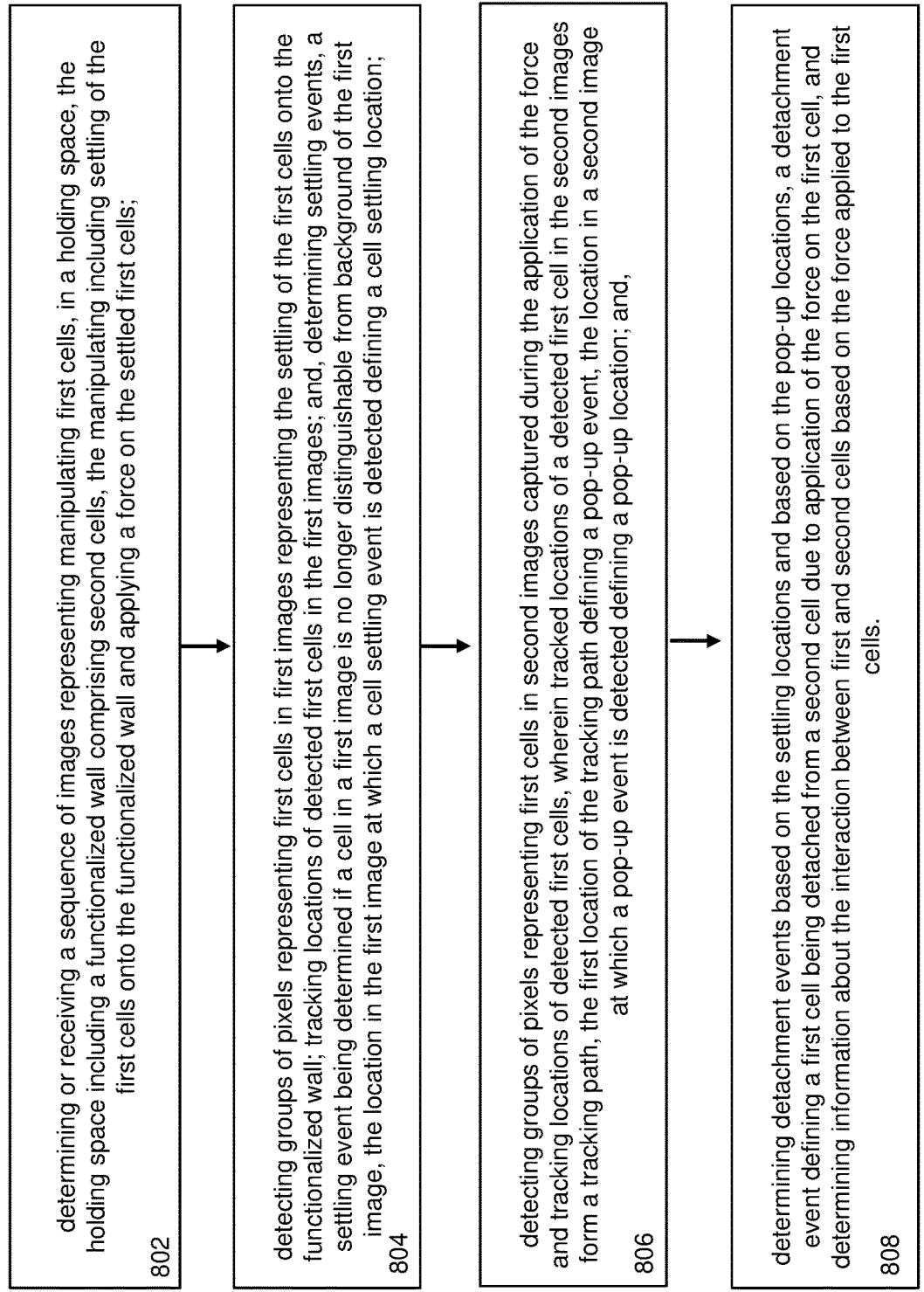
FIG. 8 depicts a flow diagram of a method for determining interaction between cells according to an embodiment of the invention.

FIG. 8 depicts a flow diagram of a method for determining interaction between cells, e.g. the cell avidity, according to an embodiment of the invention.

The method may start with a step 802 determining or receiving a sequence of images of manipulating first cells, e.g. effector cells, in a holding space, wherein the holding space may include a functionalized wall comprising second cells, e.g. target cells. Here, the target cells may be connected to the wall of the flow cell so that they will not detach when a force is applied to the functionalized wall surface. The manipulating of the cell may include settling of the first cells onto the functionalized wall. The settling of the cells allows the cells to move around over the wall in order to find a suitable target cell it can bind to. The process of settling and binding may be referred to the incubation phase. Thereafter, a force may be applied to the settled first cells.

In step 804, groups of pixels may be detected in in first images representing the settling of the first cells onto the functionalized wall. These detected groups of pixels may represent first cells. Further, tracking locations of detected first cells in the first images may be determined, wherein during tracking a cell may be classified as no longer trackable. In that case, a cell that is tracked in consecutive images becomes no longer distinguishable from background of the first image, because the cell is close to the functionalized wall surface. Such event may be referred to as a settling event. The location in the image at which a cell settling event is detected defines a cell settling location.

In a further step 806, groups of pixels may be detected in second images captured during the application of the force. These detected groups of pixels may represent first cells and tracking locations of detected first cells, wherein tracked locations of a detected first cell in the second images may form a tracking path, the first location of the tracking path defining a pop-up event, the location in a second image at which a pop-up event is detected defining a pop-up location.

Thereafter, detachment events may be determined (step 808), wherein detachment events are related to first cells being detached from the second cells due to application of the force on the first cells. These events may be determined based on the settling locations and the pop-up locations. The detachment events are then used to determine information about the interaction between first and second cells. In particular, the information about the interaction between the cells may be based on the force that was applied to the first cells when the detachment events occurred.

In an embodiment, a background correction method may be applied to the captured video images before the images are processed for cell detection and tracking. In such method, the background of the captured images (video frames), i.e. the functionalized wall comprising the target cells, may be removed based one or more captured background images. This way, the foreground information, i.e. the unbound cells, may be more clearly visible so that subsequent image processing, e.g. detection and tracking can be improved. Thus, the background correction method may be used as a pre-processing step for improving the accuracy of the detection and tracking algorithm. This background subtraction may be based on a pre-acquired image or series of images (before flush in of the first cells) and may be static (unchanging). It may however also involve a background model which is dynamically updated based on images taken during the experiment and may involve an advanced background model describing e.g. the dynamic behavior of the target cells.

Figure 9:
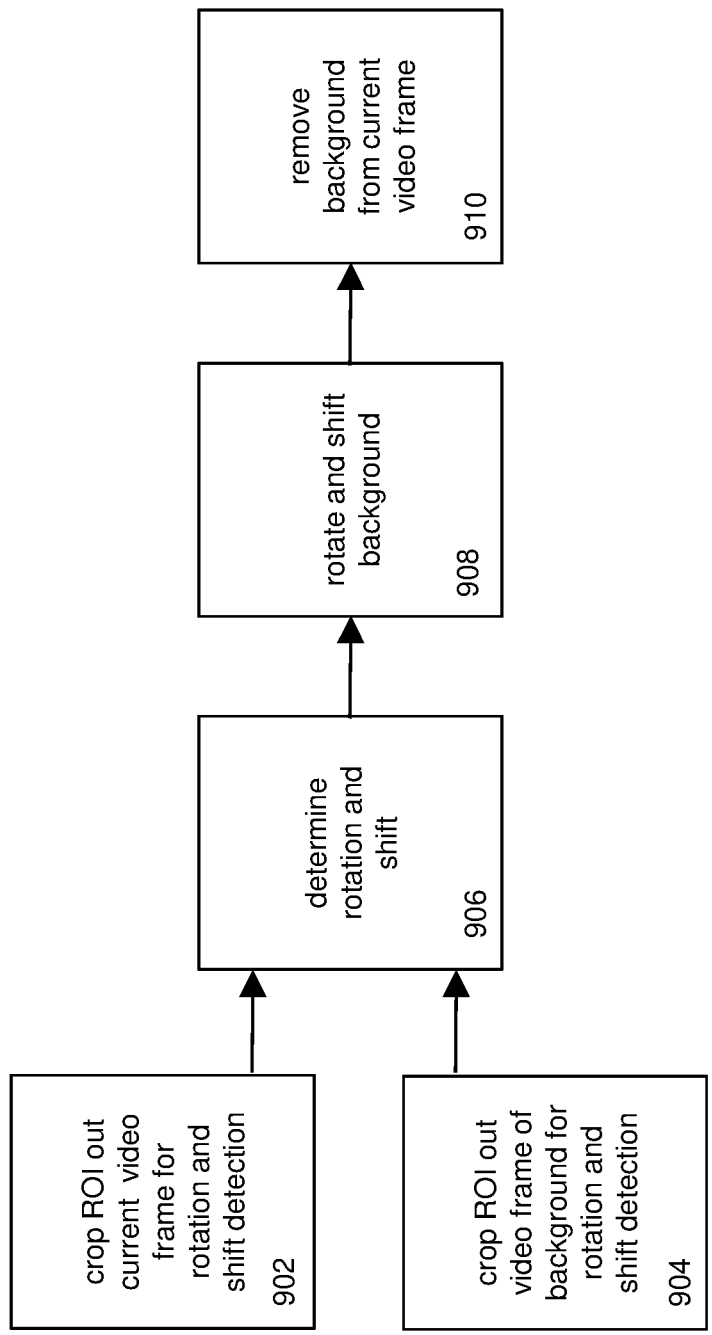
FIG. 9 depicts a background correction method according to an embodiment of the invention.

FIG. 9 depicts a background correction method according to an embodiment of the invention. In order to accurately remove the background information in the captured images, the background patterns of the background image should be accurately aligned with the background pattern of the captured images. To that end, a first region of interest (ROI) may be cropped out at a predetermined position in a captured image and at the same position in a background image (e.g. an image of the functionalized wall surface comprising target cells but no other (effector) cells) a second ROI may be cropped out (steps 902,904). A pattern matching algorithm, preferably a geometric pattern matching algorithm, or another suitable image registration method may be used to align the patterns in the first and second ROIs. The alignment information may include information about rotation and/or translation parameters that allow accurate matching of the patterns of the first and second ROI (step 906). The determined alignment information is subsequently applied to the background image (step 908) so that the aligned background image can be used to remove the background of the current image (step 910) or at least a substantial part thereof.

Instead of using a static background picture, a rolling median background correction algorithm may be used or any other suitable algorithm for dynamically correcting the background. In case if a rolling median background correction, a background image may be formed by taking the median intensity value over a predetermine number of images, e.g. 10 images, for each pixel separately or for groups of pixels. This background image may then used for removing the background of the current image (or at least a substantial part thereof).

Figure 10:
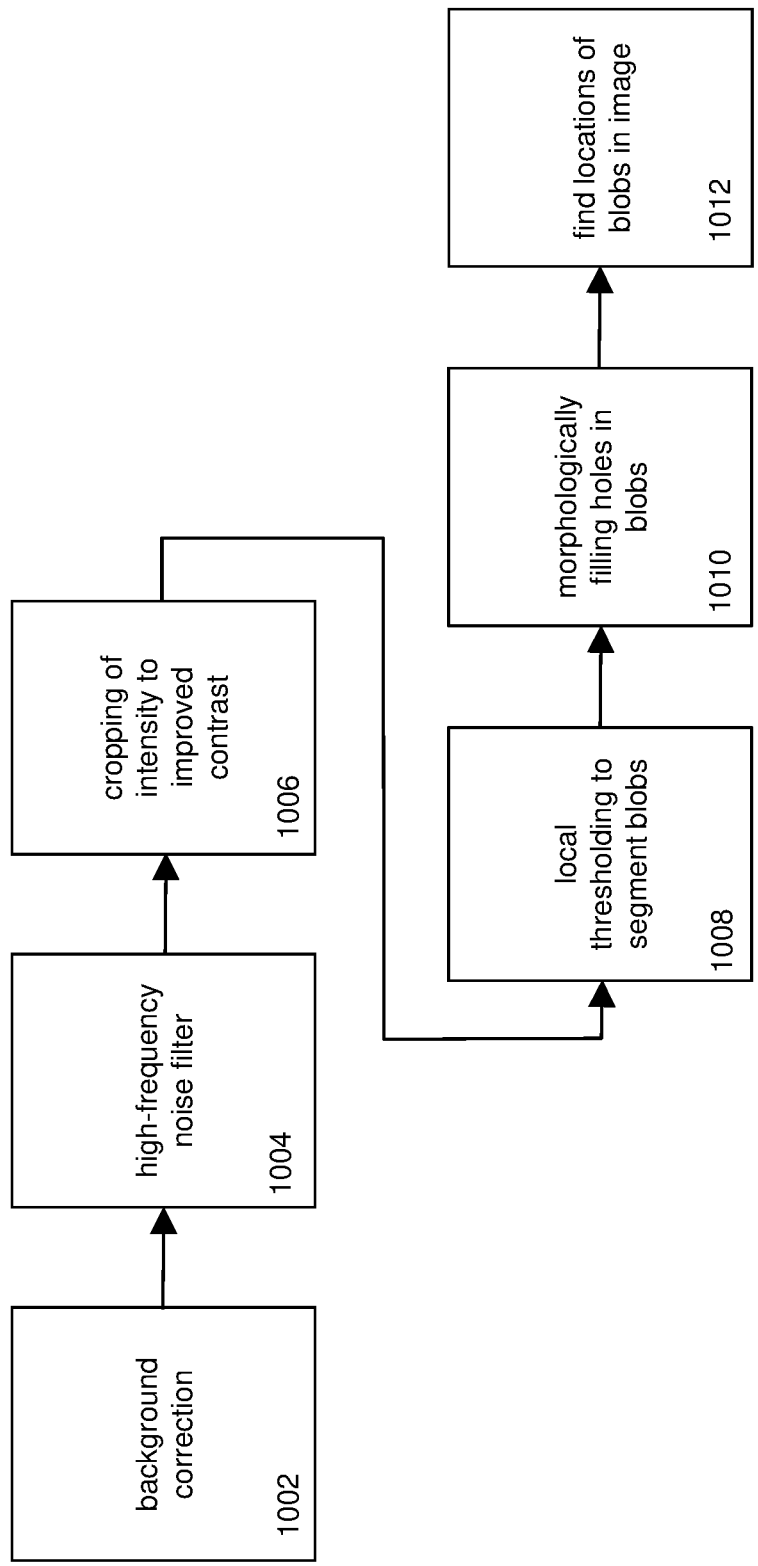
FIG. 10 depicts a cell detection method according to an embodiment of the invention.

FIG. 10 depicts a cell detection method according to an embodiment of the invention. As shown in this figure, the method may start with background correction method (step 1002) that allows removal of the background, i.e. the functionalized wall including the target cells, from the captured images so that foreground objects can better distinguished from the background. Exemplary background correction methods that may be used as described with reference to FIG. 9. One or more filters, e.g. a Laplacian or Gaussian filter, may be applied to the background corrected images (step 1004) for blurring high frequency information in the image. The intensity of the pixels may be cropped to improve the black and white saturation (step 1006). This step may be applied to ensure that the blobs in the processed image have sufficient contrast with respect to the background so that the blobs can be detected using a segmentation method (step 1008). In an embodiment, a known thresholding operation, preferably a local thresholding operation, may be used to create a binary image, wherein blobs are formed by pixels having a first value and the background is formed by pixels having a second value. Blobs that contain "holes" due to irregularities or noise may be processed so that these holes are removed by filling each of these holes with pixel values (step 1010). Finally, the location of the blobs in the image may be determined (step 1012). Optionally, the blobs may be classified based on proximity, size, intensity, area, symmetry, etc.

Figure 11:
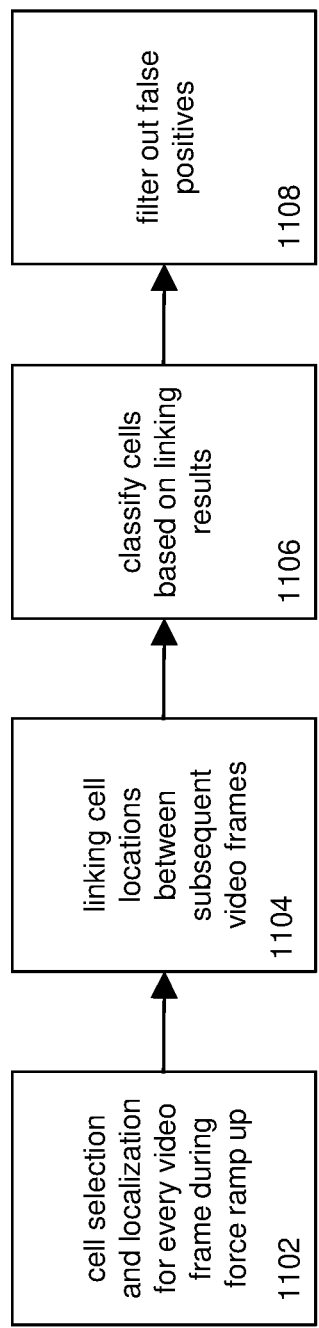
FIG. 11 depicts a method for detecting and tracking cells in images according to an embodiment of the invention.

FIG. 11 depicts a method for detecting and tracking cells in images according to an embodiment of the invention. In particular, this figure provides a flow diagram describing a method of detecting and tracking cells during a force ramp up. This process may start with cell detection and localization (step 1102) using a method as described with reference to FIG. 10. Further, locations of detected cells in subsequent images may be linked using a minimization algorithm, preferably a global minimization algorithm (step 1106). For example, to efficiently link large numbers of detected cells in subsequent images a minimization of a cost function may be used as described in the article by Jaquaman et al, Robust single-particle tracking in live-cell time-lapse sequences, Nature Methods, Vol. 8, no. 8, August 2008, pp. 295-702, which is hereby incorporated by reference in this application. The linking of the cell locations will generate tracking paths as described with reference to FIG. 5-8, which are used to determine pop-up events and which can be used to classify cells that are detected in the images into detached cells and other cells (step 1206). Further information derived from the images, e.g. non-functional areas in the functionalized wall, cluster locations and edges, may be used to further filter out pop-up events are not related to cells being detached from target cells due to the application of the force (step 1108).

Figure 12:
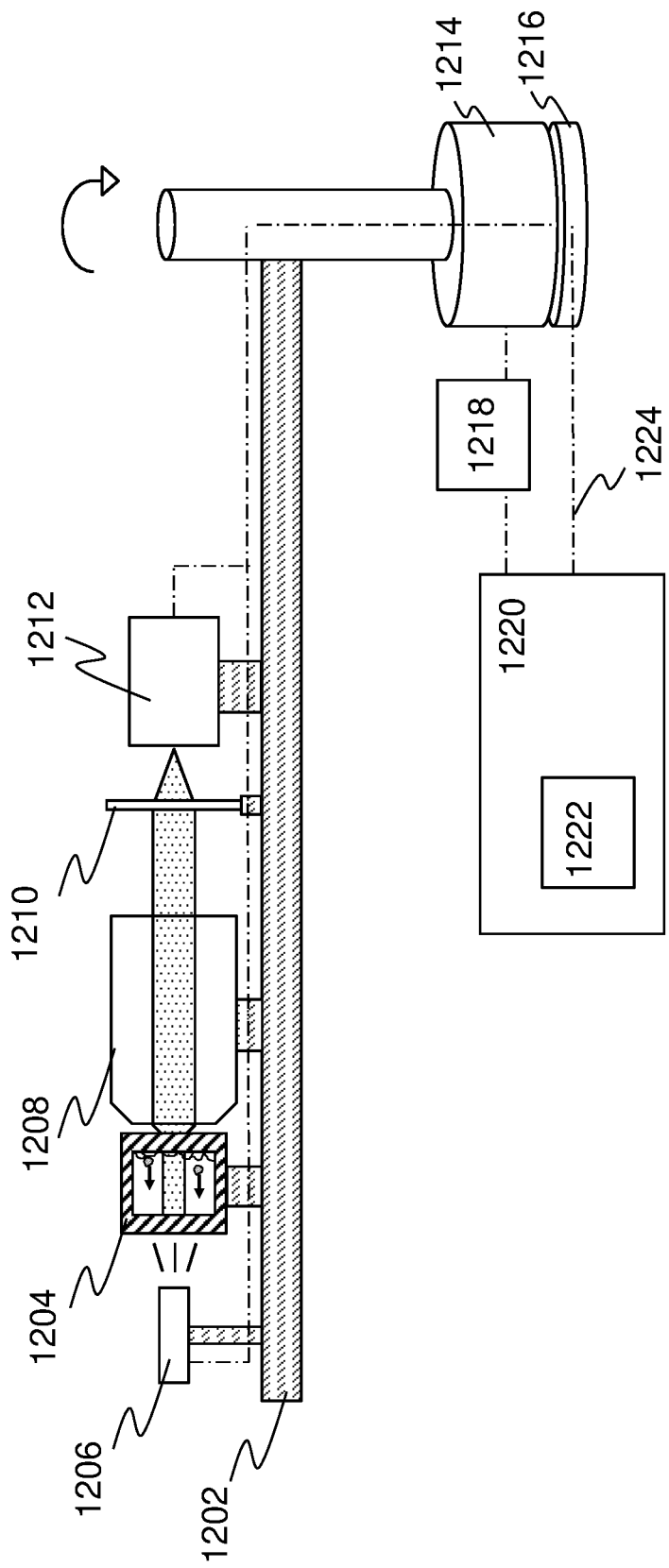
FIG. 12 depicts a schematic of a force spectroscopy system according to another embodiment of the invention.

FIG. 12 schematically depicts a further force spectroscopy system configured to capture images of a force spectroscopy experiment. This system includes a rotary arm 1202 that is rotatable mounted onto a rotor system that includes a rotor 1214 and a rotary joint 1216. A holding space 1204, e.g. a microfluidic cell, comprising cells (e.g. effector cells and target cells attached to a functionalized wall of the holding space) may be mounted onto the rotary arm. Further, a light source 1206, an adjustable objective 1208, a tube lens 1210 and a camera 1212 may form an imaging system for capturing images of effector cells interacting with target cells. A rotor controller 1218 may be used to control the rotor system to spin the rotary arm in a circular motion so that a centrifugal force is exerted onto the effector cells. The system may be connected to a computer 1220 that includes a processing module 1222 that is configured to control the rotor controller and the imaging system. Further, when in use, the computer may receive captured images 1224 of the holding space while a force ramp is exerted onto effector cells. Further, the processing module is configured to process the captures images in a similar way as described with reference to FIG. 3-11 above. Exemplary embodiments of such force spectroscopy systems are described in WO2017/147398 and U.S. Pat. No. 8,795,143 which hereby incorporated by reference into this application.

Figure 13:
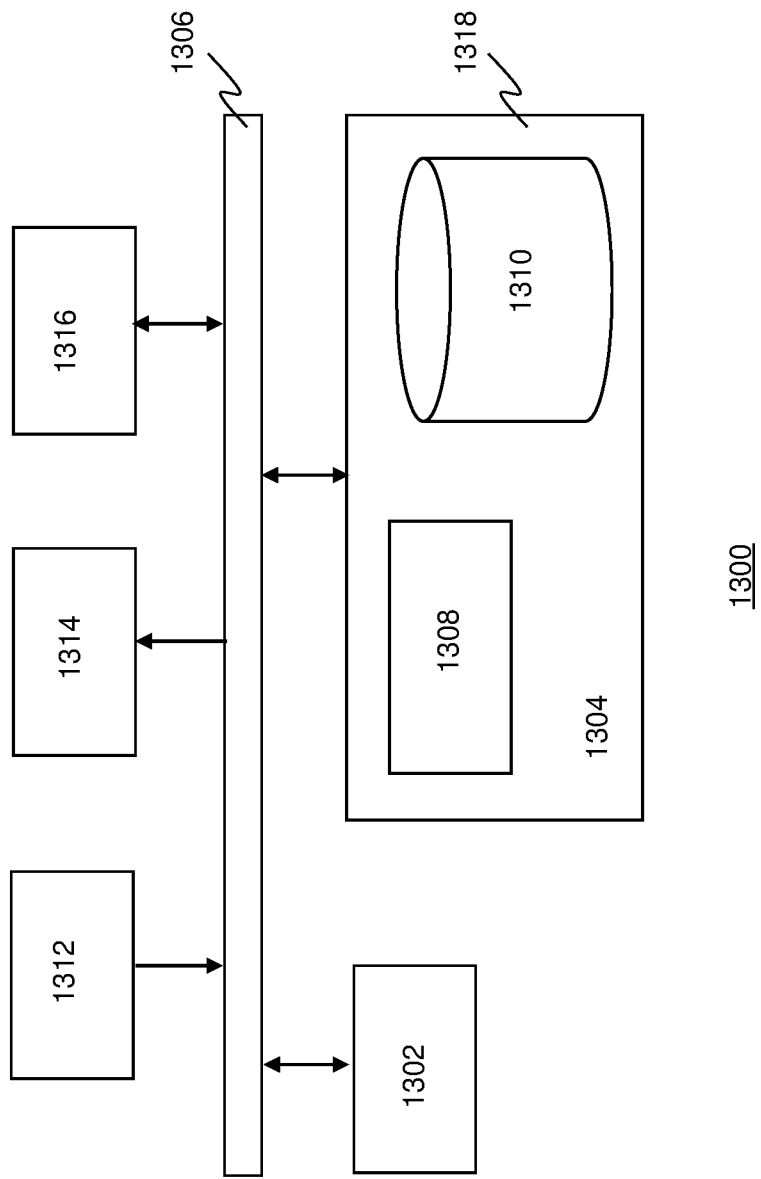
FIG. 13 is a block diagram illustrating an exemplary data processing system that may be used for executing methods and software products described in this application.

FIG. 13 is a block diagram illustrating exemplary data processing systems described in this disclosure. Data processing system 1300 may include at least one processor 1302 coupled to memory elements 1304 through a system bus 1306. As such, the data processing system may store program code within memory elements 1304. Further, processor 1302 may execute the program code accessed from memory elements 1304 via system bus 1306. In one aspect, data processing system may be implemented as a computer that is suitable for storing and/or executing program code. It should be appreciated, however, that data processing system 1300 may be implemented in the form of any system including a processor and memory that is capable of performing the functions described within this specification.

Memory elements 1304 may include one or more physical memory devices such as, for example, local memory 1308 and one or more bulk storage devices 1310. Local memory may refer to random access memory or other non-persistent memory device(s) generally used during actual execution of the program code. A bulk storage device may be implemented as a hard drive or other persistent data storage device. The processing system 1300 may also include one or more cache memories (not shown) that provide temporary storage of at least some program code in order to reduce the number of times program code must be retrieved from bulk storage device 1310 during execution.

Input/output (I/O) devices depicted as input device 1312 and output device 1314 optionally can be coupled to the data processing system. Examples of input device may include, but are not limited to, for example, a keyboard, a pointing device such as a mouse, or the like. Examples of output device may include, but are not limited to, for example, a monitor or display, speakers, or the like. Input device and/or output device may be coupled to data processing system either directly or through intervening I/O controllers. A network adapter 1316 may also be coupled to data processing system to enable it to become coupled to other systems, computer systems, remote network devices, and/or remote storage devices through intervening private or public networks. The network adapter may comprise a data receiver for receiving data that is transmitted by said systems, devices and/or networks to said data and a data transmitter for transmitting data to said systems, devices and/or networks. Modems, cable modems, and Ethernet cards are examples of different types of network adapter that may be used with data processing system 1300.

As pictured in FIG. 13, memory elements 1304 may store an application 1318. It should be appreciated that data processing system 1300 may further execute an operating system (not shown) that can facilitate execution of the application. Application, being implemented in the form of executable program code, can be executed by data processing system 1300, e.g., by processor 1302. Responsive to executing application, data processing system may be configured to perform one or more operations to be described herein in further detail.

In one aspect, for example, data processing system 1300 may represent a client data processing system. In that case, application 1318 may represent a client application that, when executed, configures data processing system 1300 to perform the various functions described herein with reference to a "client". Examples of a client can include, but are not limited to, a personal computer, a portable computer, a mobile phone, or the like.

In another aspect, data processing system may represent a server. For example, data processing system may represent an (HTTP) server in which case application 1318, when executed, may configure data processing system to perform (HTTP) server operations. In another aspect, data processing system may represent a module, unit or function as referred to in this specification.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A method for determining interaction between cells comprising:
    determining or receiving a sequence of images representing manipulating first cells, in a holding space, the holding space including a functionalized wall comprising second cells, the manipulating including settling of the first cells onto the functionalized wall and applying a force on the settled first cells;
    detecting groups of pixels representing the first cells in first images representing the settling of the first cells onto the functionalized wall; and, tracking locations of the detected first cells in the first images; and, determining settling events, a settling event being determined if a cell is no longer distinguishable from the background, the location in the first image at which a cell settling event is detected defining a cell settling location;
    detecting groups of pixels representing first cells in second images captured during the application of the force and tracking locations of the detected first cells, wherein tracked locations of the detected first cells in the second images form a tracking path, the first location of the tracking path defining a pop-up event, the location in a second image at which a pop-up event is detected defining a pop-up location; and,
    determining detachment events based on the settling locations and based on the pop-up locations, a detachment event defining a first cell being detached from a second cell due to application of the force on the first cell, and determining information about the interaction between the first and the second cells based on the force applied to the first cells.

2. The method according to claim 1 wherein the determining of the detachment events includes:
    determining a distance between one said settling location and one said pop-up location and determining one said detachment event based on a threshold value.

3. The method of claim 2, wherein the detachment event is determined if the distance between the settling location and the pop-up location is smaller than the threshold value.

4. The method according to claim 1, wherein classification into a trackable or non-trackable cell is based on at least one of: intensity values of pixels of the group of pixels representing a cell; a shape, texture and/or dimensions of the group of pixels representing a cell; and/or, a contrast ratio between pixel values of group of the pixels representing a cell and pixel values representing the background of an image in which the group of pixels is tracked.

5. The method according to any claim 1, wherein the determining if a cell is no longer distinguishable from the background is based on at least one of: one or more changes in pixel values of a group of pixels representing a cell, a shape, texture and/or, a contrast ratio between pixel values of the group of pixels representing a cell and pixel values representing the background of an image in which the group of pixels is tracked.

6. The method of claim 5, wherein the changes in the pixel values include changes of intensity values.

7. The method according to claim 1, wherein the determining of the images includes:
    determining or receiving one or more background images of the functionalized wall comprising the second cells; and
    removing the background from the images representing the manipulation of the first cells by using the one or more background images.

8. The method according to claim 1, wherein the determining of the detachment events includes:
    determining or receiving locations of one or more non-functional areas in the images of the functionalized wall surface, a non-functional area defining an area of the functionalized wall surface from which the second cells are absent; and
    disregarding one said pop-up location in the determining of detachment events if the pop-up location is located in or within a predetermined distance of the one or more non-functional areas.

9. The method according to claim 1, wherein the determining of the detachment events includes:
    determining or receiving one or more cluster locations in the images captured during the application of the force, a cluster defining an aggregation of cells which are not bound to the functionalized cell surface in the images when the force is applied to the first cells; and
    disregarding one said pop-up location in the determining of detachment events if the pop-up location is detected within one of the one or more cluster locations.

10. The method according to claim 1, wherein the determining of the detachment events includes:
    disregarding one said pop-up location in the determining of detachment events if the pop-up location is located within a predetermined distance of the edges of the images.

11. The method according to claim 1, wherein tracking the location of each detected cell includes:
    linking positions of detected cells in subsequent images using a minimization technique.

12. The method according to claim 1, wherein the method further includes:
determining an avidity curve based on the detachment events and the force associated with each of the detachment events.

13. The method according to claim 1, wherein the first cells are effector cells and the second cells are target cells.

14. The method according to claim 1, wherein first cells include at least one of: lymphocytes, monocytic cells, granulocytes, T cells, natural killer cells, B-Cells, CAR-T cells, dendritic cells, Jurkat cells, bacterial cells, red blood cells, macrophages, TCR Tg T-cells, OT-I/OT-II cells, splenocytes, thymocytes, BM derived hematopoietic stem cells, TILs, tissue derived macrophages, and innate lymphoid cells; and/or, the second cells include at least one of: tumor cells, stem cells, epithelial cells, B16 melanoma, fibroblasts, endothelial cells, HEK293, HeLa, 3T3, MEFs, HuVECs, microglia, and neuronal cells.

15. A computer program or suite of computer programs comprising at least one software code portion or a computer program product storing at least one software code portion, the software code portion, when run on a computer system, being configured for executing the method steps according to claim 1.

16. The method according to claim 1, wherein the determining of the detachment events includes:
determining or receiving one or more cluster locations in the images captured during the application of the force, a cluster defining an aggregation of cells which are not bound to the functionalized cell surface in the images when the force is applied to the first cells; and
disregarding one said pop-up location in the determining of detachment events if the pop-up location is detected within a predetermined distance of one of the one or more cluster locations.

17. The method according to claim 1, wherein the second cells are effector cells and the first cells are target cells.

18. A module for analyzing images of cells being manipulated in a holding space, the module comprising a non-transitory computer readable storage medium having computer readable program code embodied therewith, and a processor coupled to the computer readable storage medium, wherein responsive to executing the computer readable program code, the processor is configured to perform executable operations comprising:
determining or receiving a sequence of images representing manipulating first cells, in the holding space, the holding space including a functionalized wall comprising second cells, the manipulating including settling of the first cells onto the functionalized wall and applying a force on the settled first cells;
detecting groups of pixels representing the first cells in first images representing the settling of the first cells onto the functionalized wall; and, tracking locations of detected first cells in the first images; and, determining settling events, a settling event being determined if a cell is no longer distinguishable from the background, the location in the first image at which one said cell settling event is detected defining a cell settling location;
detecting groups of pixels representing the cells in second images captured during the application of the force and tracking locations of detected cells, wherein tracked locations of detected cells in the second images form a tracking path, the first location of the tracking path defining a pop-up event, the location in a second image at which a pop-up event is detected defining a pop-up location; and,
determining detachment events based on the settling locations and based on the pop-up locations, a detachment event defining one said first cell being detached from one said second cell due to application of the force on the first cell, and determining information about the interaction between the first and the second cells based on the force applied to the first cells.

19. A system for determining interaction between cells comprising:
a sample holder comprising a holding space for cells;
a force generator for applying a force to the cells;
an imaging system capturing images of the cells in the holding space;
a controller module for controlling the force generator and the imaging system;
a non-transitory computer readable storage medium having computer readable program code embodied therewith, and a processor coupled to the computer readable storage medium, wherein responsive to executing the computer readable program code, the processor is configured to perform executable operations comprising:
determining or receiving a sequence of images representing manipulating first cells, in the holding space, the holding space including a functionalized wall comprising second cells, the manipulating including settling of the first cells onto the functionalized wall and applying a force on the settled first cells;
detecting groups of pixels representing the first cells in first images representing the settling of the first cells onto the functionalized wall; tracking locations of detected first cells in the first images; and, determining settling events, a settling event being determined if one said cell is no longer distinguishable from background of the first image, the location in the image at which one said cell settling event is detected defining a cell settling location;
detecting groups of pixels representing the cells in second images captured during the application of the force and tracking locations of detected cells, wherein the tracked locations of detected cells in the second images form a tracking path, the first location of the tracking path defining a pop-up event, the location in a second image at which the pop-up event is detected defining a pop-up location; and,
determining detachment events based on the settling locations and based on the pop-up locations, a detachment event defining one said first cell being detached from one said second cell due to application of the force on the first cell, and determining information about the interaction between first and second cells based on the force applied to the first cells.

* * * * *